United States Patent [19]

Lüthi et al.

[11] Patent Number: 4,468,352
[45] Date of Patent: Aug. 28, 1984

[54] DISTYRYLBIPHENYLS

[75] Inventors: Christian Lüthi, Basel; Hans R. Meyer, Binningen; Kurt Weber, Basel, all of Switzerland

[73] Assignee: Ciba-Geigy Corporation, Ardsley, N.Y.

[21] Appl. No.: 372,779

[22] Filed: Apr. 28, 1982

Related U.S. Application Data

[62] Division of Ser. No. 137,147, Apr. 4, 1980, Pat. No. 4,339,393.

[30] Foreign Application Priority Data

Apr. 11, 1979 [CH] Switzerland .................. 3478/79
Jun. 26, 1979 [CH] Switzerland .................. 5952/79

[51] Int. Cl.³ .................. C07C 141/02; C07C 93/02; C07D 211/00; C07D 207/06
[52] U.S. Cl. .................. 260/459 A; 260/459 R; 260/501.15; 260/501.18; 260/501.21; 260/239 B; 260/924; 544/85; 544/87; 560/9; 560/10; 560/42; 560/172; 560/173; 564/282; 564/285; 564/286; 564/288; 564/337; 546/190; 546/191; 546/266; 546/267; 548/523
[58] Field of Search .............. 260/459 A, 459 R, 924, 260/501.15, 501.18, 465 E, 239 B, 239 BF, 501.21; 544/87; 546/190, 191, 258; 564/266, 353, 354, 286, 337, 282, 285, 288; 560/39, 42, 173, 9, 172, 10; 542/464, 459

[56] References Cited

U.S. PATENT DOCUMENTS

| | | | |
|---|---|---|---|
| 3,755,446 | 8/1973 | Sheuermann et al. | 564/156 |
| 3,843,718 | 8/1974 | Lüthi | 564/156 |
| 4,009,193 | 2/1977 | Sheuermann et al. | 260/459 A |
| 4,263,431 | 4/1981 | Weber et al. | 260/924 |

FOREIGN PATENT DOCUMENTS

| | | | |
|---|---|---|---|
| 1793482 | 3/1972 | Fed. Rep. of Germany | 260/505 R |
| 2209128 | 9/1972 | Fed. Rep. of Germany | 564/156 |

*Primary Examiner*—Nicky Chan
*Attorney, Agent, or Firm*—Edward McC. Roberts

[57] ABSTRACT

The distyrylbiphenyls of the formula

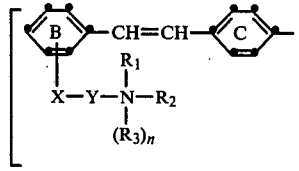
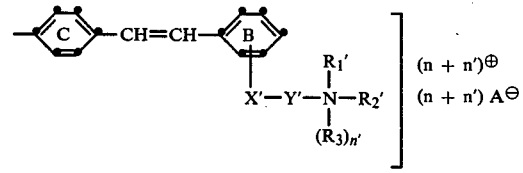

in which X and X' independently of one another are a direct bond, oxygen, sulfur, —O—$C_{1-3}$-alkylene-CON($R_4$)——CON($R_4$)—, —O—$C_{1-3}$-alkylene-COO—, OCO or —COO—, with the proviso that if n+n'=0, X and X' may not be —CON($R_4$)— or O—$C_{1-3}$-alkylene-CON($R_4$)—, and if n+n'=2 and X and X' are —CON($R_4$)— or —COO—, $A^\ominus$ may not be a phosphite or phosphonate anion, and Y and Y' independently of one another are $C_{1-20}$-alkylene, $R_1$ and $R_1'$ independently of one another are unsubstituted or substituted $C_{1-8}$-alkyl or $C_{3-4}$-alkenyl, or $R_1$ together with $R_2$, or $R_1'$ together with $R_2'$, is a heterocyclic ring, $R_2$ and $R_2'$ independently of one another are unsubstituted or substituted $C_{1-8}$-alkyl or $C_{3-4}$-alkenyl, or $R_2$ together with $R_1$, or $R_2'$ together with $R_1'$, is a heterocyclic ring, or $R_1$ and $R_2$, or $R_1'$ and $R_2'$, together with $R_3$ are a pyridine or picoline ring, $R_3$ is hydrogen, unsubstituted or substituted $C_{1-4}$-alkyl or $C_{3-4}$-alkenyl or together with $R_1$ and $R_2$, or with $R_1'$ and $R_2'$, is a pyridine or picoline ring, $R_4$ is hydrogen or unsubstituted or substituted $C_{1-6}$-alkyl, $A^\ominus$ is a colorless anion and n and n' independently of one another are the number 0 or 1, and the benzene nuclei B and C can also be substituted by non-chromophoric substituents, can be prepared by reacting a correspondingly substituted benzaldehyde with a biphenyl phosphonate and then alkylating or protonating the distyrylbiphenyldiamine formed. The distyrylbiphenyls are fluorescent brightening agents for organic materials. They are particularly suitable for use as additives for textile and laundry after-treatment agents which contain cationic textile softeners.

7 Claims, No Drawings

DISTYRYLBIPHENYLS

This is a divisional of application Ser. No. 137,147 filed on Apr. 4, 1980, now U.S. Pat. No. 4,339,393.

The present invention relates to novel distyrylbiphenyls, a process for their preparation and their use for the fluorescent brightening of organic materials.

Water-soluble distyrylbiphenyls with anionic substituents in the benzene nuclei have been disclosed in the literature, for example in German Auslegeschrift No. 1,793,482, but these compounds are not compatible with cationic textile assistants. Certain distyrylbiphenyls with cationic substituents are also known, but, despite their cationic character, these lead to unsatisfactory results when they are used in a cationic medium.

Distyrylbiphenyls have now been found which do not have these disadvantages.

Accordingly, the invention relates to novel distyrylbiphenyls of the formula

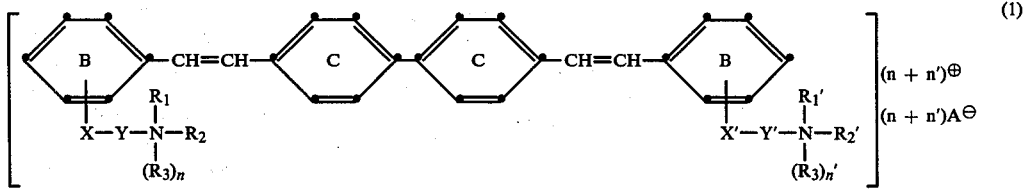

(1)

in which X and X' independently of one another are a direct bond, oxygen, sulfur, —O—$C_{1-3}$-alkylene—CON($R_4$)—, —CON($R_4$)—, —O—$C_{1-3}$-alkylene—COO—, —OCO— or —COO—, with the proviso that if n+n'=0, X and X' may not be —CON($R_4$) or —O—$C_{1-3}$-alkylene—CON($R_4$)—, and if n+n'=2 and X and X' are —CON($R_4$)— or —COO—, $A^\ominus$ may not be a phosphite or phosphate anion, and Y and Y' independently of one another are $C_{1-20}$-alkylene, $R_1$ and $R_1'$ independently of one another are unsubstituted or substituted $C_{1-8}$-alkyl or $C_{3-4}$-alkenyl, or $R_1$ together with $R_2$, or $R_1'$ together with $R_2'$, is a heterocyclic ring, $R_2$ and $R_2'$ independently of one another are unsubstituted or substituted $C_{1-8}$-alkyl or $C_{3-4}$-alkenyl, or $R_2$ together with $R_1$, or $R_2'$ together with $R_1'$, is a heterocyclic ring, or $R_1$ and $R_2$, or $R_1'$ and $R_2'$, together with $R_3$ are a pyridine or picoline ring, $R_3$ is hydrogen, unsubstituted or substituted $C_{1-4}$-alkyl or $C_{3-4}$-alkenyl or together with $R_1$ and $R_2$, or with $R_1'$ and $R_2'$, is a pyridine or picoline ring, $R_4$ is hydrogen or unsubstituted or substituted $C_{1-6}$-alkyl, $A^\ominus$ is a colourless anion and n and n' independently of one another are the number 0 or 1, and the benzene nuclei B and C can also be substituted by non-chromophoric substituents.

The alkylene radicals Y and Y' can be different and straight-chain or branched and preferably have 1 to 12 and especially 1 to 6 C atoms and can also carry a hydroxyl group.

Suitable alkyl radicals $R_1$, $R_1'$, $R_2$ and $R_2'$ are those having 1 to 8 and preferably 1 to 4 C atoms. These radicals and also alkyl radicals $R_3$ can be straightchain or branched and can be substituted, for example by cyano, hydroxyl, alkoxy, phenyl or alkoxycarbonyl having 1 to 4 C atoms. $R_1$, $R_1'$, $R_2$ and $R_2'$ can also be substituted by chlorine.

The radicals $R_1$ and $R_2$ together, and also the radicals $R_1'$ and $R_2'$ together, can each form a 5-membered to 7-membered heterocyclic ring, for example a piperidine, pyrrolidine, hexamethyleneimine, pyridine, triazole, imidazole or morpholine ring, which can be substituted by alkyl groups having 1 to 4 C atoms.

An alkyl radical $R_4$ preferably has 1 to 4 C atoms and can be substituted, for example, by cyano, carbamoyl, carbalkoxy, hydroxyl, halogen or alkoxy having 1 to 4 C atoms.

Examples of non-chromophoric substitutents of the benzene rings B and C are: halogen atoms, such as chlorine and bromine; $C_{1-4}$-alkyl groups, $C_{5-7}$-cycloalkyl groups; $C_{3-4}$-alkenyl groups; $C_{1-4}$-alkoxy groups, $C_{3-4}$-alkenyloxy groups; sulfonyl groups, for example $C_{1-4}$-alkyl- or phenyl-sulfonyl groups; $C_{2-6}$-carbalkoxy groups; carbamoyl groups and sulfamoyl groups and also the substituents required to make up a fused carbocyclic 5-membered or 6-membered ring.

Distyrylbiphenyls according to the invention which are worthy of particular mention are those of the formula

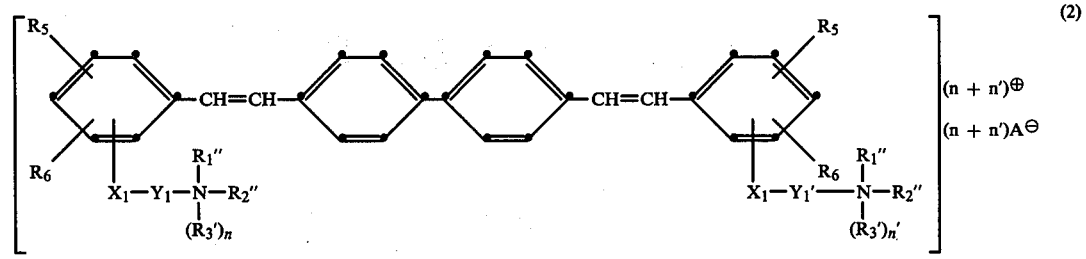

(2)

in which $X_1$ is a direct bond, oxygen, sulfur, —O—$C_{1-3}$-alkylene—CONH—, —CONH—, —O—$C_{1-3}$-alkylene—COO—, —OCO— or —COO—, with the proviso that if n+n'=0, $X_1$ may not be —O—$C_{1-3}$-alkylene—CONH— or —CONH—, and if n+n'=2 and $X_1$ is —CONH— or —COO—, $A^\ominus$ may not be phosphite or phosphonate anions, and $Y_1$ and $Y_1'$ independently of one another are $C_{1-4}$-alkylene or hydroxypropylene, $R_1''$ and $R_2''$ independently of one another are $C_{1-4}$-alkyl, together are a pyrrolidine, piperidine, hexamethyleneimine or morpholine ring, or together with $R_3'$ are a pyridine or picoline ring, $R_3'$ is hydrogen, $C_{1-4}$-alkyl, $C_{3-4}$-alkenyl, $C_{1-3}$-alkoxycarbonylmethyl, benzyl, $C_{2-4}$-hydroxyalkyl, $C_{2-4}$-cyanoalkyl, or together with $R_1''$ and $R_2''$ is a pyridine or picoline ring, $R_5$ is hydrogen, chlorine, $C_{1-4}$-alkyl, $C_{3-4}$-alkenyl or $C_{1-3}$-alkoxy, or together with $R_6$ is a trimethylene or tetramethylene group, $R_6$ is hydrogen, chlorine, $C_{1-4}$-alkyl

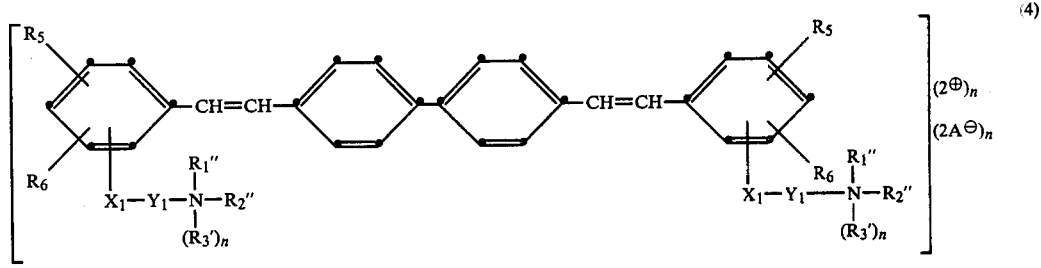

or $C_{1-3}$-alkoxy, or together with $R_5$ is a trimethylene or tetramethylene group, n and n' independently of one another are the number 0 or 1 and $A^\ominus$ is a colourless anion.

Preferred distyrylbiphenyls of the formulae (1) and (2) are those which are symmetrical, i.e. in which $X=X'$, $Y=Y'$ and $Y_1=Y_1'$, $R_1=R_1'$, $R_2=R_2'$ and $n=n'$; in which X and X' are not —CON($R_4$)—, —O—$C_{1-3}$-alkylene—CON($R_4$)— or —COO— and $X_1$ is not —CONH—, —O—$C_{1-3}$-alkylene—CONH— or —COO—; which are quaternised, i.e. in which n and n' are the number 1, and in which $X_1$ is in the 2-position and $R_3'$ is $C_{1-3}$-alkyl.

In distyrylbiphenyls of the formula (2), alkyl and alkoxy substitutents $R_5$ and $R_6$ are preferably methyl and methoxy.

Particularly preferred distyrylbiphenyls are those of the formula

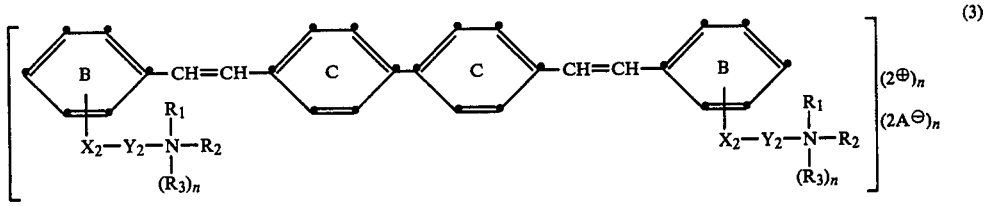

in which $X_2$ is oxygen, sulfur, —CON($R_4$)—, —OCO— or —COO—, with the proviso that if $n=0$, $X_2$ may not be —CON($R_4$)—, and if $X_2$ is —CON($R_4$)— or —COO—, $A^\ominus$ may not be phosphite or phosphonate anions, and $Y_2$ is $C_{1-20}$-alkylene, $R_1$ is unsubstituted or substituted $C_{1-8}$-alkyl or $C_{3-4}$-alkenyl, together with $R_2$ is a heterocyclic ring, or together with $R_2$ and $R_3$ is a pyridine or picoline ring, $R_2$ is unsubstituted or substituted $C_{1-8}$-alkyl or $C_{3-4}$-alkenyl, or together with $R_1$ is a heterocyclic ring, or toegether with $R_1$ and $R_3$ is a pyridine or picoline ring, $R_3$ is hydrogen, unsubstituted or substituted $C_{1-4}$-alkyl, $C_{3-4}$-alkenyl or together with $R_1$ and $R_2$ is a pyridine or picoline ring, $R_4$ is hydrogen or unsubstituted or substituted $C_{1-6}$-alkyl, n is the number 0 or 1 and $A^\ominus$ is a colourless anion, and the benzene nuclei B and C can also be substituted by non-chromophoric substituents; those of the formula in which $X_1$ is a direct bond, oxygen, sulfur, —O—$C_{1-3}$-alkylene—CONH—, —CONH—, —O—$C_{1-3}$-alkylene—COO, —OCO— or —COO—, with the proviso that if $n=0$, $X_1$ may not be —O—$C_{1-3}$-alkylene—CONH— or —CONH—, and if $n=1$ and $X_1$ is —CONH— or —COO—, $A^\ominus$ may not be phosphite or phosphonate anions, and $Y_1$ is $C_{1-4}$-alkylene or hydroxypropylene, $R_1''$ and $R_2''$ independently of one another are $C_{1-4}$-alkyl, together are a pyrrolidine, piperidine, hexamethyleneimine or morpholine ring, or together with $R_3'$ are a pyridine or picoline ring, $R_3'$ is hydrogen, $C_{1-4}$-alkyl, $C_{3-4}$-alkenyl, $C_{1-3}$-alkoxycarbonylmethyl, benzyl, $C_{2-4}$-hydroxyalkyl, $C_{2-4}$-cyanoalkyl, or together with $R_1''$ und $R_2''$ is a pyridine or picoline ring, $R_5$ is hydrogen, chlorine, $C_{1-4}$-alkyl, $C_{3-4}$-alkenyl or $C_{1-3}$-alkoxy, or together with $R_6$ is a trimethylene or tetramethylene group, $R_6$ is hydrogen, chlorine, $C_{1-4}$-alkyl or $C_{1-3}$-alkoxy, or together with $R_5$ is a trimethylene or tetramethylene group, n is the number 0 or 1 and $A^\ominus$ is a colourless anion, and those of the formula

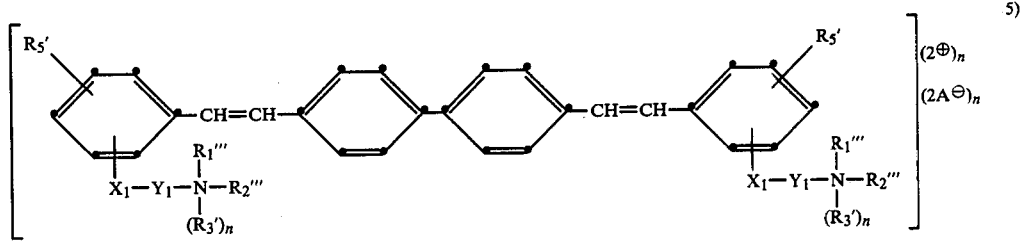

in which $X_1$ is a direct bond, oxygen, sulfur, —O—$C_{1-3}$-alkylene—CONH—, —CONH—, —O—$C_{1-3}$-alkylene—COO—, —OCO— or —COO—, with the proviso that if $n=0$, $X_1$ may not be —O—$C_{1-3}$-alkylene—CONH— or —CONH—, and if $n=1$ and $X_1$ is —CONH— or —COO—, $A^\ominus$ may not be phosphite or phosphonate anions, and $Y_1$ is $C_{1-4}$-alkylene or hydroxypropylene, $R_1''$ and $R_2''$ independently of one another are $C_{1-4}$-alkyl, together are a pyrrolidine, piperdine or morpholine ring, or together with $R_3'$ are a pyridine ring, $R_3'$ is hydrogen, $C_{1-4}$-alkyl, $C_{3-4}$-alkenyl, $C_{1-3}$-alkoxycarbonylmethyl, benzyl, $C_{2-4}$-hydroxyalkyl or $C_{2-4}$-cyanoalkyl, or together with $R_1'''$ and $R_2'''$ is a pyridine ring, $R_5'$ is hydrogen, chlorine, $C_{1-4}$-alkyl or $C_{1-3}$-alkoxy, n is the number 0 or 1 and $A^\ominus$ is a colourless anion.

In the formulae (3), (4), (5) and (6), $X_1$ and $X_2$ are preferably in the 2-position and are not $-CON(R_4)-$, $-O-C_{1-3}$-alkylene$-CONH-$ or $-CONN-$, or $-OCO-$; $R_3'$ and $R_3''$ are $C_{1-3}$-alkyl; n is 1 and $A^\ominus$ is $CH_3OSO_3^\ominus$, $C_2H_5OSO_3^\ominus$, $Cl^\ominus$, $Br^\ominus$, $CH_3COO^\ominus$, $HCOO^\ominus$ or

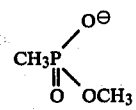

Important distyrylbiphenyls are (A) those of the formula

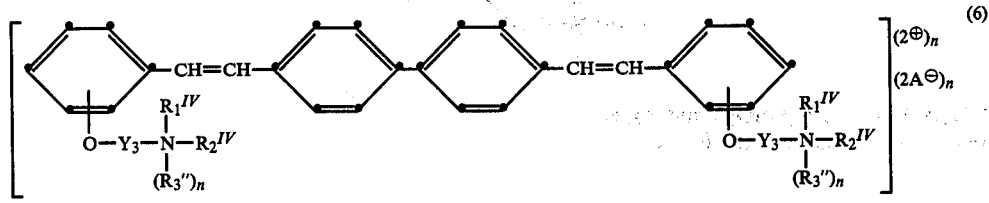

in which $Y_3$ is $C_{2-4}$-alkylene, $R_1^{IV}$ is $C_{1-3}$-alkyl, or together with $R_2^{IV}$ is a pyrrolidine, piperidine, hexamethyleneimine or morpholine ring, $R_2^{IV}$ is $C_{1-3}$-alkyl, or together with $R_1^{IV}$ is a pyrrolidine, piperidine, hexamethyleneimine or morpholine ring, $R_3''$ is hydrogen or $C_{1-3}$-alkyl, n is the number 0 or 1 and $A^\ominus$ is a colourless anion, (B) those of the formula

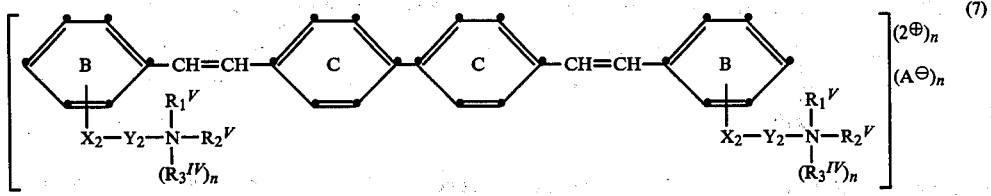

in which $X_2$ is oxygen, sulfur, $$-CON-\atop R_4$$

or $-COO-$, with the proviso that if $A^\ominus$ is a phosphite or phosphonate anion, $X_2$ is not $-CON(R_4)-$ or $-COO-$, and $Y_2$ is alkylene having 2–20 C atoms, $R_1^V$ is unsubstituted or substituted alkyl having 1–8 C atoms or alkenyl having 2–4 C atoms, or together with $R_2^V$ is a heterocyclic ring, $R_2^V$ is unsubstituted or substituted alkyl having 1–8 C atoms or alkenyl having 2–4 C atoms, or together with $R_1^V$ is a heterocyclic ring, $R_3^{IV}$ is hydrogen or unsubstituted or substituted alkyl having 1–4 C atoms, $R_4$ is hydrogen or unsubstituted or substituted alkyl having 1–6 C atoms, $A^\ominus$ is the equivalent of a colourless anion and n is the number 0 or 1, and the benzene nuclei B and C can also be substituted by non-chromophoric substituents, (C) those of the formula

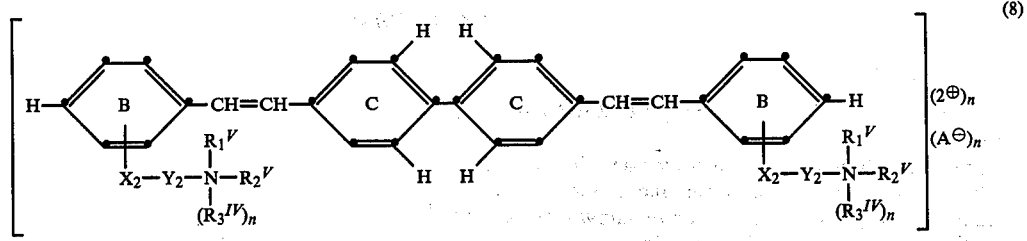

in which $X_2$, $Y_2$, $R_1^V$, $R_2^V$, $R_3^{IV}$, $A^\ominus$, n and the benzene nuclei B and C are as defined above, and (D) those of the formula

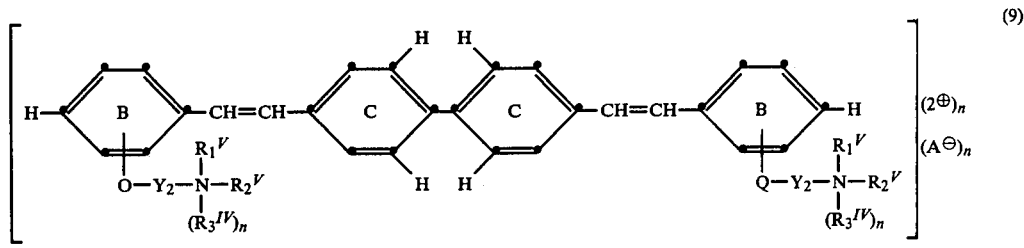

in which $Y_2$, $R_1^V$, $R_2^V$, $R_3^{IV}$, $A^\ominus$, n and the benzene nuclei B and C are as defined above.

Particularly preferred distyrylbiphenyls are those of the formulae

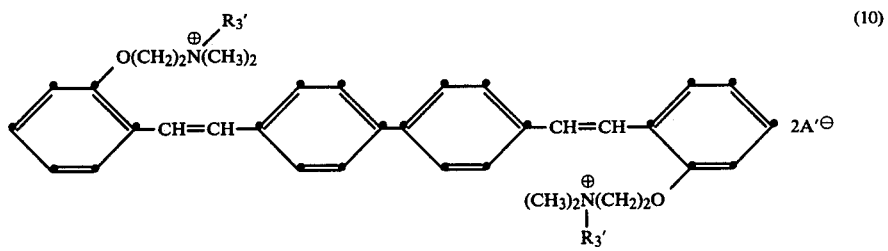

in which $A'^\ominus$ is $CH_3OSO_3^\ominus$ or $C_2H_5OSO_3^\ominus$ and $R_3'$ is methyl or ethyl, and

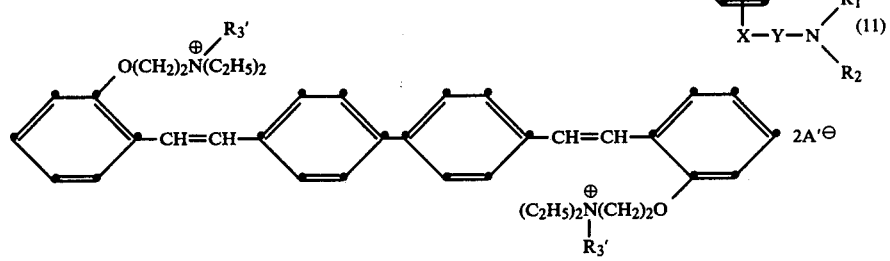

in which $A'^\ominus$ is $CH_3OSO_3^\ominus$ or $C_2H_5OSO_3^\ominus$ and $R_3'$ is methyl or ethyl, and especially those of the formula

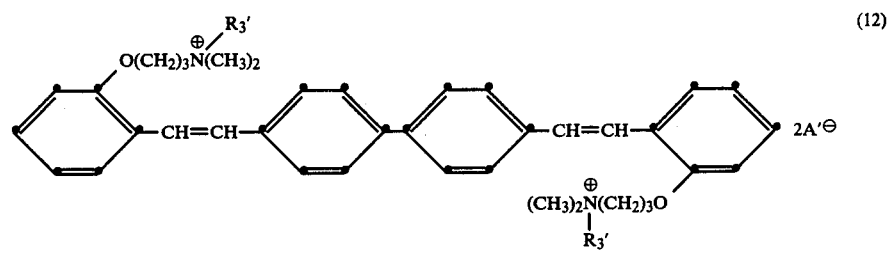

in which $A'^\ominus$ is $CH_3OSO_3^\ominus$ or $C_2H_5OSO_3^\ominus$ and $R_3'$ is methyl or ethyl.

The distyrylbiphenyls of the formula (1) in which X is a direct bond, oxygen or sulfur and n and n' are the number 0 are prepared in a manner known per se, by reacting a compound of the formula

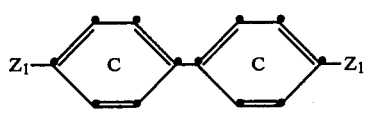

in a molecular ratio of 1:2 with one of the two compounds of the formulae

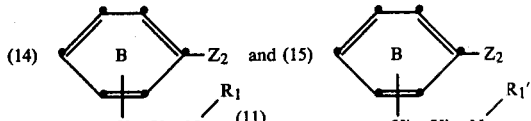

or with a mixture of these two compounds, in the presence of a strong base, in which formulae the benzene nuclei B and C can also be substituted by non-chromophoric substituents, X and X' are a direct bond, oxygen or sulfur and Y, Y', $R_1$, $R_1'$, $R_2$ and $R_2'$ are as defined above and one of the symbols $Z_1$ and $Z_2$ is a OCH group and the other is a grouping of the formula

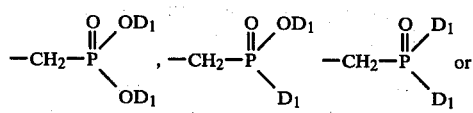 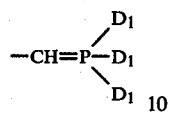

in which $D_1$ is an unsubstituted or substituted alkyl, aryl, cycloalkyl or aralkyl radical, and then quaternising or protonising the resulting compound of the formula

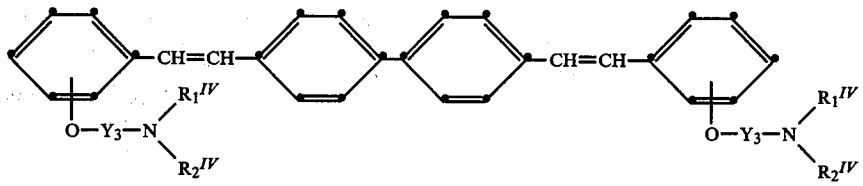

in which $D_1$ is an unsubstituted or substituted alkyl, aryl, cycloalkyl or aralkyl radical, and, if desired, quaternising or protonising the resulting compound of the formula

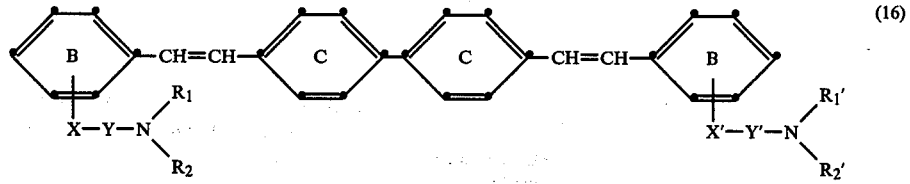

in which $Y_3$, $R_1^{IV}$ and $R_2^{IV}$ are as defined above, using 2 mol equivalents of an alkylating agent or, respectively, of an acid of the formula $R_3''$-A, in which $R_3''$ and A are as defined above.

(16)

in which X, X', Y, Y', $R_1$, $R_1'$, $R_2$ and $R_2'$ are as defined and the benzene nuclei B and C can also be substituted by non-chromophoric substituents, in a manner known per se, using 1 to 2 mol equivalents of an alkylating agent or, respectively, of an acid of the formula $R_3$-A, in which $R_3$ and A are as defined above.

Distyrylbiphenyls of the formula (6) are prepared by reacting a compound of the formula

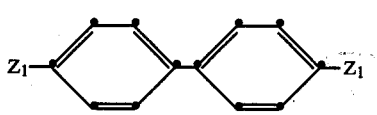

in a molecular ratio of 1:2 with a compound of the formula

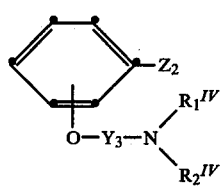

in the presence of a strong base, in which formulae $Y_3$, $R_1^{IV}$ and $R_2^{IV}$ are as defined above and one of the symbols $Z_1$ and $Z_2$ is a OCH group and the other is a grouping of the formula

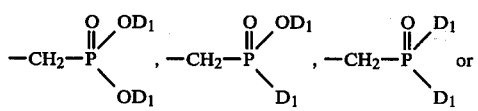

The condensation reaction is advantageously carried out in inert solvents. Examples of such solvents are hydrocarbons, such as toluene and xylene, or alcohols, such as methanol, ethanol, isopropanol and butanol, glycols, glycol ethers, such as 2-methoxyethanol, hexanols, cyclohexanol and cyclooctanol, and also ethers, such as diisopropyl ether, tetrahydrofuran and dioxan, and also dimethylsulfoxide, formamide and N-methylpyrrolidone. Polar organic solvents such as dimethylformamide and dimethylsulfoxide are particularly suitable. Some of the reactions can also be carried out in aqueous solution.

The temperature at which the reaction is carried out can vary within wide limits. It is determined:

(α) by the stability of the solvent used towards the reactants, especially towards the strongly basic alkali metal compounds, (β) by the reactivity of the reactants participating in the condensation reaction and (γ) by the effectiveness of the solvent/base combination as a condensing agent.

In practice, accordingly, in general temperatures between about 10° and 100° C. are suitable. If dimethylformamide is used as the solvent, the preferred temperature range is from 20° to 60° C.

Suitable strongly basic alkali metal compounds are, in particular, the hydroxides, amides and alcoholates (preferably with alcohols containing 1 to 4 carbon atoms) of the alkali metals, and for economic reasons the hydroxides, amides and alcoholates of lithium, sodium and potassium are of predominant interest. In principle, however, and in special cases alkali metal sulfides and alkali metal carbonates, aryl-alkali metal compounds, for example phenyl-lithium, or strongly basic amines (including ammonium bases), for example trialkylammonium hydroxides, can also be used successfully.

The starting materials of the formula (14) or (15) in which $Z_2$ is an aldehyde group are obtained, for example, by alkylating hydroxybenzaldehydes with dialkylaminoalkyl chlorides in the presence of basic alkali metal compounds or alkaline earth metal compounds, for example sodium alcoholates (see Example 1), potassium carbonate, sodium carbonate, calcium carbonate, magnesium oxide, sodium hydride, potassium hydroxide or sodium hydroxide, in inert organic solvents, such as alcohols or dialkylamides of aliphatic carboxylic acids. Particularly suitable solvents are anhydrous solvents which can also be used in the subsequent stage, i.e. for the preparation of the compounds of the formula (16), for example dimethylformamide, and in this case it is no longer necessary to isolate the compounds of the formula (14) or (15).

Distyrylbiphenyls of the formula

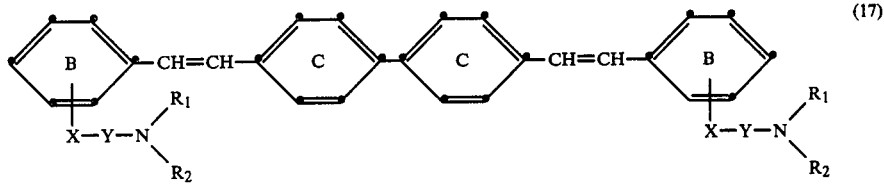
(17)

in which X is —O—$C_{1-3}$-alkylene—CON($R_4$)—, —O—$C_{1-3}$-alkylene—COO—,

or —COO— are prepared in a manner known per se from the corresponding acids (cf. German Auslegeschriften Nos. 1,793,482 and 2,209,128), by preparing the acid halides in a manner known per se and reacting these halides with a compound of the formula HN($R_4$)—Y—N($R_1$)($R_2$) or HOY—N($R_1$)($R_2$).

Distyrylbiphenyls of the formula

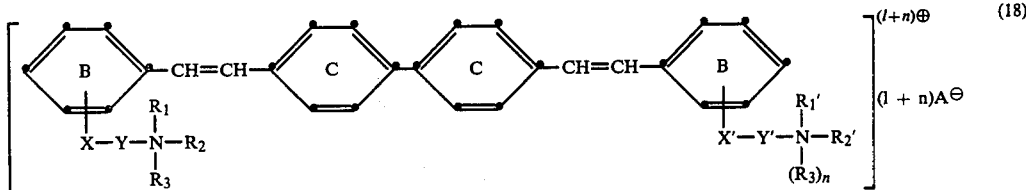
(18)

in which X and X' are a direct bond, oxygen, sulfur, —O—$C_{1-3}$-alkylene—CON($R_4$)—, —O—$C_{1-3}$-alkylene—COO—,

—OCO— or —COO—, with the proviso that if $A^\ominus$ is a phosphite or phosphonate anion, X is not —CON($R_4$)— or —COO—, and Y and Y' are alkylene having 1-20 C atoms, $R_1$ and $R_1'$ are unsubstituted or substituted alkyl having 1-8 C atoms or alkenyl having 2-4 C atoms, or $R_1$ together with $R_2$, or $R_1'$ together with $R_2'$, is a heterocyclic ring, $R_2$ and $R_2'$ are unsubstituted or substituted alkyl having 1-8 C atoms or alkenyl having 2-4 C atoms, or $R_2$ together with $R_1$, or $R_2'$ together with $R_1'$, is a heterocyclic ring, $R_3$ is hydrogen, unsubstituted or substituted alkyl having 1-4 C atoms or $C_{3-4}$-alkenyl, $R_4$ is hydrogen or unsubstituted or substituted alkyl having 1-6 C atoms, $A^\ominus$ is a colourless anion and n is the number 0 or 1, and the benzene nuclei B and C can also be substituted by non-chromophoric substituents, are prepared by quaternising or protonising distyrylbiphenyls of the formula (16) in a manner known per se, using 1 to 2 mol equivalents of an alkylating agent or, respectively, of an acid of the formula $R_3$-A, in which formulae the benzene nuclei B and C, and X, X', Y, Y', $R_1$, $R_1'$, $R_2$, $R_2'$, $R_3$, n and A are as defined above.

Suitable quaternising and protonising agents $R_3$-A are, for example, the following compounds: alkyl halides, such as methyl iodide, ethyl iodide, ethyl bromide or butyl bromide, or benzyl chloride, dialkyl sulfates, such as dimethyl sulfate or diethyl sulfate, sulfonic acid esters, such as methyl toluenesulfonate, ethyl toluenesulfonate, methyl benzenesulfonate or ethyl benzenesulfonate, alkylene oxides, such as ethylene oxide or propylene oxide, or epichlorohydrin, the compounds of the formula

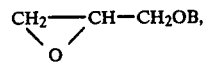

in which B is methyl, ethyl, propyl, butyl or phenyl, and phosphites or phosphonates of the formula

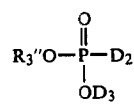

in which $R_3''$ is alkyl having 1-4 C atoms and $D_2$ is hydrogen or alkyl which is unsubstituted or substituted by hydroxyl, cyano, alkylcarbonyloxy or alkoxycarbonyl, each having 1 to 4 C atoms in the alkyl moiety, and $D_3$ is alkyl having 1 to 4 C atoms.

The quaternisation of the compounds of the formula (16) with alkyl halides, dialkyl sulfates or sulfonic acid esters to give the compounds of the formula (1) is advantageously carried out in a solvent which is inert towards the alkylating agent. Examples of suitable solvents are hydrocarbons, such as benzene, toluene and xylene, halogenated aliphatic or aromatic hydrocarbons, such as chloroform, ethylene chloride, chlorobenzene and dichlorobenzene, alcohols, such as ethanol and butanol, ethylene glycol and ethylene glycol monomethyl ether, ethers, such as ethylene glycol dimethyl ether and dioxan, or amides, such as dimethylformamide and N-methylpyrrolidone. Sometimes it also proves advantageous to use the quaternising agent as the solvent. Quaternisation with the said alkylating agents is advantageously carried out at temperatures between 0° and 180° C. and preferably at 30° to 140° C.

The quaternisation of the compounds of the formula (16) with alkylene oxides or epichlorohydrin or its derivatives of the formula

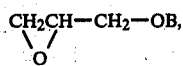

in which B is as defined, to give the compounds of the formula (1), is carried out at the indicated temperatures in an acid medium, advantageously in the presence of an organic acid, such as formic acid, acetic acid, propionic acid or lactic acid; however, inorganic acids, such a sulfuric acid, phosphoric acid or hydrogen halide acids can also be used for this purpose. These inorganic acids can be used in the concentrated, commercially available form, in the form of dilute aqueous solutions or as a mixture with the said organic solvents, if desired with the addition of water. If the reaction is carried out in the presence of organic acids, these acids are usually used in the concentrated form, if desired as a mixture with the said organic solvents.

Preferred phosphites and phosphonates are, for example, dimethyl phosphite, diethyl phosphite, dimethyl methanephosphonate, diethyl methanephosphonate, methyl ethyl methanephosphonate, methyl propyl methanephosphonate, methyl butyl methanephosphonate, methyl hexyl methanephosphonate, methyl octyl methanephosphonate, methyl decyl metanephosphonate, methyl dodecyl methanephosphonate, dimethyl 3-hydroxy-ethanephosphonate, dimethyl 3-acetoxyethanephosphonate, dimethyl 3-methoxycarbonylethanephosphonate and dimethyl 3-cyanethanephosphonate. The reaction is carried out in water and/or organic solvents such as methanol, ethanol, propanol, isopropanol, butanol, glycol, glycol methyl ether, glycol dimethyl ether, glycol butyl ether, diglycol methyl ether, methyl ethyl ketone, methyl butyl ketone, dimethylformamide, sulfolane, hydroxypropionitrile, toluene, xylene, benzyl alcohol, phenoxyethanol or benzyloxypropionitrile, at preferably 60° to 190° C. When liquid quaternising agents are used, the reaction can also be carried out in the absence of an additional solvent.

If protonated compounds of the formula (1), i.e. acid addition salts, are desired, the protonising agents used are in particular mineral acids. In principle, all strong to medium strength organic acids or mineral acids are suitable.

Suitable solvents in which the protonisation can be carried out are, in general, all inert solvents. Preferred solvents are those which dissolve the starting material and from which the end product precipitates immediately. Examples are: aromatic hydrocarbons, such as benzene, toluene and xylene; halogenated hydrocarbons, such as trichloroethane, tetrachloroethylene, chlorobenzene or dichlorobenzene, and also nitro compounds, such as nitromethane, nitropropane or nitrobenzene, alkanols and open or cyclic ethers, such as butanol, dibutyl ether, ethylene glycol, ethylene glycol monomethyl ether, ethylene glycol monoethyl ether, anisole or dioxan; ketones, such as cyclohexanone or methyl ethyl ketone; fatty acid amides, such as dimethylformamide or dimethylacetamide; sulfoxides, such as dimethylsulfoxide, and carboxylic acid esters, such as ethyl acetate or butyl acetate.

Distyrylbiphenyls of the formula (1) in which $X = X'$ and is the grouping —OCO— and $n = n'$ and is the number 1 can be prepared, for example, from the corresponding phenols, by reacting these with a halogenoacyl halide and quaternising the resulting reaction product with a trialkylamine or pyridine of the formula $N(R_1)(R_2)(R_3)$; in the starting material and the reaction product $Y = Y'$, $R_1 = R_1'$ and $R_2 = R_2'$ and these symbols and $R_3$ are as defined above. The quaternisation is advantageously effected in an inert solvent using at least 2 mols of the amine at 50° to 160° C. and preferably at 80°–130° C.

The novel compounds defined above exhibit a more or less pronounced fluorescence in solution or dispersion. They can be used for the fluorescent brightening of a wide variety of synthetic, regenerated man-made or natural organic materials or substances which contain such organic materials.

The organic materials which are to undergo fluorescent brightening can be in the most diverse states of processing (raw materials, semi-finished goods or finished goods).

The compounds to be used according to the invention are of importance, inter alia, for the treatment of textile organic materials, especially textile fabrics.

Depending on the type of fluorescent brightener compound used, it can prove advantageous to carry out the treatment in a neutral or alkaline or acid bath.

The novel fluorescent brightening agents of the present invention can also be used for the fluorescent brightening of paper pulps, inter alia in the presence of, for example, cationic retention agents and other additives.

The novel fluorescent brightening agents of the present invention can be employed in the following use forms:

(a) in mixtures with dyes (shading) or pigments (coloured pigments or especially, for example, white pigments) or as an additive to dyebaths;

(b) in mixtures with wetting agents, plasticisers, swelling agents or antioxidants;

(c) in combination with diverse textile finishing processes, for example flameproof finishes, soft-handle finishes, anti-soiling finishes or antistatic finishes, or antimicrobial finishes;

(d) incorporation of the fluorescent brightening agents into polymer carriers (polymerisation, polycondensation or polyaddition products), in dissolved or dispersed form, for use, for example, in coating agents, impregnating agents or binders (solutions, dispersions and emulsions) for textiles, non-wovens, paper and leather;

(e) as additives to a wide variety of industrial products in order to render these more marketable (for example improving the appearance of soaps, detergents, soft-rinsing agents and textile treatment agents and pigments);

(f) in combination with other fluorescent brightening substances;

(g) in spinning bath preparations, i.e. as additives to spinning baths such as are used for improving the slip for the further processing of synthetic fibres, or from a special bath before stretching the fibre, for example as an after-treatment of wet-spun polyacrylic fibres in the so-called gel state;

(h) for various purposes of a photographic nature, for example for electrophotographic reproduction or supersensitising; and (i) depending on the substitution, as laser dyes.

If the brightening process is combined with textile treatment or finishing methods, the combined treatment can in many cases advantageously be carried out with the aid of appropriate stable preparations which contain the fluorescent brightener compounds in a concentration such that the desired white effect is achieved.

The amount of the novel fluorescent brightening agents to be used according to the invention, based on the material to undergo fluorescent brightening, can vary within wide limits. A marked and lasting effect can be obtained even with very small amounts and in certain cases, for example, with amounts of 0.0001 percent by weight. However, it is also possible to use amounts of up to about 0.8 percent by weight and, in some cases, of up to about 2 percent by weight. For most practical purposes, it is preferable to use amounts between 0.0005 and 0.5 percent by weight.

For various reasons it is often advantageous not to use the brighteners on their own, i.e. in the pure form, but to use them in the form of a mixture with a wide variety of assistants and extenders.

The novel fluorescent brightening agents are particularly suitable for use as additives to wash liquors or to heavy duty and domestic detergents and laundering after-treatment agents, to which they can be added in various ways. They are advantageously added to wash liquors in the form of their solutions in water or organic solvents, or, in a finely divided form, as aqueous dispersions. They are advantageously added to domestic or heavy duty detergents at any stage of the production process for the detergents. They can be added either in the form of a solution or dispersion in water or other solvents or, without assistants, as a dry brightener powder. For example, the fluorescent brightening agents can be dissolved in the detergent substances or can be mixed, kneaded or ground with the substances and, in this form, admixed with the finished detergent. However, they can also be sprayed in a dissolved or pre-dispersed form onto the finished detergent.

The compounds according to the invention can also be used in a rinsing liquor, such as is customary for merely imparting a soft handle, antistatic properties, anti-soiling effects, fragrances and the like. In particular, they are suitable for use in laundry after-treatment agents which contain cationic softeners.

The present invention therefore also relates to a detergent, which is preferably in the liquid form and which also contains, in addition to the novel distyryl-biphenyls and the customary additives, nonionic surfactants and cationic textile softeners.

Suitable nonionic surfactants are those which are commercially available, for example the water-soluble products which are obtained by adding an alkylene oxide or an equivalent compound containing a reactive hydrogen onto a hydrophobic compound. The hydrophobic organic products can be heterocyclic compounds and in particular aliphatic compounds or aromatic compounds. Preferred compounds are higher aliphatic alcohols and alkylphenols, but it is also possible to use other compounds, for example carboxylic acids, carboxamides, mercaptans, sulfamides and the like. Preferred nonionic compounds are the adducts of ethylene oxide with higher aliphatic alcohols having 6 to 50 or more C atoms. The amount of ethylene oxide can vary within wide limits, but in general at least 5 mols of ethylene oxide are used per mol of hydrophobic substance. Other lower alkylene oxides, for example propylene oxide and butylene oxide, can be used in place of all or part of the ethylene oxide. Other nonionic compounds which can be used are:

(a) polyoxyalkylene esters of organic acids, such as higher fatty acids, resin acids, tall oil acids and acids of the oxidation products of mineral oil, the esters of which as a rule have 10 to 22 C atoms in the acid moiety and contain about 12 to about 30 mols of ethylene oxide or its equivalent; and (b) alkylene oxide adducts of higher fatty acid amides, in which the fatty acid moiety as a rule has 8 to 22 C atoms and has been subjected to a condensation reaction with 10 to 50 mols of ethylene oxide. The corresponding carboxamides and sulfamides can likewise be used as substantially equivalent compounds.

The nonionic surfactants used in the preparation of liquid, concentrated detergents are preferably oxalkylated higher aliphatic alcohols, the fatty alcohols having at least 6 and preferably at least 8 C atoms. Preferred alcohols are lauryl alcohol, myristyl alcohol, cetyl alcohol, stearyl alcohol and oleyl alcohol, and these are subjected to a condensation reaction with at least 6 mols of ethylene oxide. A typical nonionic product is the adduct of an aliphatic alcohol having 12–13 C atoms with about 6.5 mols of ethylene oxide. After a condensation reaction with ethylene oxide, the corresponding alkylmercaptans can also be used as nonionic surfactants.

The alkoxylated higher aliphatic alcohols are particularly suitable for domestic detergents since they are readily bio-degradable and are readily compatible with cationic surfactants and textile softeners and the other additives.

Suitable cationic textile softeners are, in particular, quaternary derivatives of ammonia and/or of imidazoline with 2 long-chain aliphatic radicals, for example 1-methyl-1-oleylamidoethyl-2-oleyl-imidazolinium. X$^\ominus$, 1-methyl-1-tallow-amidoethyl-2-tallow-imidazolinium. X$^\ominus$, di-tallow-dimethyl-ammonium. X$^\ominus$ and a compound of the formula

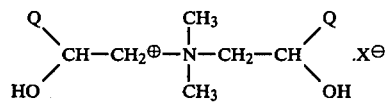

in which Q is $C_{14-16}$-alkyl and X$^\ominus$ is a chloride, bromide, methylsulfate, ethylsulfate, methanesulfonate, ethanesulfonate or toluenesulfonate anion.

The quaternary textile softeners which can be used according to the invention, and especially those mentioned above, impart to the fabric a soft and fluffy handle and, at the same time, make it easy to redampen. These textile softeners are substantive to the fabric and contribute to reducing the static charge and the tendency to crease, so that the fabric can be ironed more easily and is more pleasant to wear.

The liquid medium for the detergents according to the invention is aqueous and can consist of water alone or of water and additional solvents for certain additives. Up to 20%, and preferably up to 15%, of the total amount of solvent can be made up by the additional solvents. Suitable additional solvents are: lower alkanols or a lower diol or polyol, for example ethanol, isopropanol, ethylene glycol, propylene glycol and glycerol. Etherified polyols, such as diethylene glycol, ethylene glycol dimethyl ether and ethylene glycol monoethyl ether, can also be used as additional solvents.

The liquid detergent according to the invention can contain diverse selected compatible additives, such as soil-suspending agents, or greying inhibitors, for example polyvinyl alcohol and hydroxypropylmethylcellulose; foam inhibitors and preservatives, for example sodium benzoate; UV absorbers and perfumes. These are, of course, so chosen that they are compatible with the main components of the detergent.

The nonionic surfactants are employed in amounts of 10 to 70% by weight and preferably of 60% by weight. The concentration of the textile softener is 1 to 30% by weight and preferably 21% by weight. The aqueous solvent, which is preferably water which can also contain mono-, di- and poly-hydric alcohols and similar solvents, make up 5 to 60% by weight. The liquid or pulverulent ready-for-use detergent contains the compounds according to the invention in amounts of 0.005 to 3% by weight. The content of other assistants preferably make up less than 5% by weight of the detergent, since the use of larger amounts can influence the properties of liquid detergents. Although the preferred detergent preparation according to the application is a stable, clear liquid, a compatible opacifying agent can be added to produce an opaque appearance.

The detergent according to the invention can be used in soft or suitably hard water at elevated temperature. This detergent can also be used for washing textiles in very hard water at a lower temperature. The hardness of the water can therefore vary between 0 and more than 300 ppm, calculated as calcium carbonate, and the washing temperature can be 4° to 60° C.

The detergent according to the invention dissolves very readily in cold or warm water, cleans thoroughly, eliminates the static charge and makes the laundry soft without rendering it hydrophobic. The preferred detergent is in the form of a clear, stable liquid which retains its activity and uniformity over a prolonged period. For the preparation of clear, liquid detergents, the concentration of the active substances can be varied only within certain limits. Thus, for example, the concentration of the textile softener should not be much higher than 30% if it desired to obtain a clear, liquid detergent.

The compounds according to the invention are added in amounts of 0.005 to 1% or more, based on the weight of the finished liquid or pulverulent detergent or textile treatment agent. Wash/treatment liquors which contain the indicated amounts of the fluorescent brighteners claimed impart a brilliant appearance in daylight when used to wash textiles made of cellulose fibres, polyamide fibres, resin-finished cellulose fibres, polyester fibres, wool and the like.

The washing treatment is carried out, for example, as follows: the indicated textiles are treated for 1 to 30 minutes at 20° to 100° C. in a wash liquor which contains 0.1 to 10 g/kg of a composite detergent, containing a builder, and 0.05 to 1%, based on the weight of the detergent, of the fluorescent brighteners claimed. The liquor ratio can be 1:3 to 1:50. After washing, the textiles are rinsed and dried in the conventional manner.

In the examples, parts are by weight unless stated otherwise and percentages are always by weight. Unless indicated to the contrary, melting points and boiling points are uncorrected and frequently are not sharp, especially in the case of the quaternised compound.

EXAMPLE 1

After displacing the air by nitrogen, 22.2 g of a methanolic 30.4% solution of sodium methylate are added dropwise, with stirring, to a solution of 20.6 g of 4,4'-bis-(dimethoxy-phosphono-methyl)-biphenyl (purity 96.9%) and 24.2 g of the compound of the formula

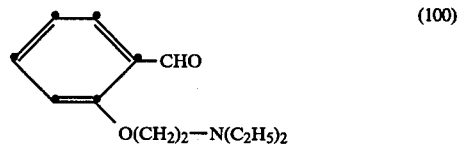

(purity 96%) in 230 ml of dimethylformamide at a rate such that the temperature does not rise above 40° C. The temperature is kept at 40°–45° C. for 2 hours, the reaction mixture is cooled with ice-water and 23 ml of water are added. The product which has precipitated is filtered off with suction, washed repeatedly with methanol and water and dried in vacuo at 90° C. 27.6 g of the compound of the formula

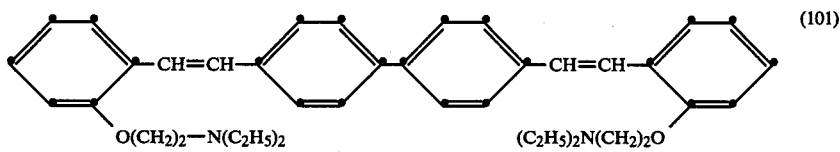

are obtained in the form of luminous, pale yellow crystals with a melting point of 127°–128° C. (after recrystallisation from nonane and n-propanol).

The compound of the formula (100) can be prepared as follows: after displacing the air by nitrogen, 732 g of a methanolic 30.7% solution of sodium methylate are added dropwise, with stirring, to a suspension of 244 g of salicylaldehyde and 344 g of 2-diethylamino-ethyl chloride hydrochloride in 2,000 ml of chlorobenzene, whereupon the suspension becomes yellow coloured and thick. The temperature is raised gradually to about 131° C. and during this step the methanol is distilled off. The reaction mixture is kept at this temperature for a further 4 hours and allowed to cool, 500 ml of water are added, the two layers are separated and the organic phase is dried over sodium sulfate. The solvent is then evaporated off under a water pump vacuum and the residue is subjected to fractional distillation under a high vacuum. After separating off a small amount of first runnings, 327.5 g of a slightly reddish liquid with a boiling point of 105°–118°/0.06 mbar and a purity of 96% are obtained.

The compounds of the formula

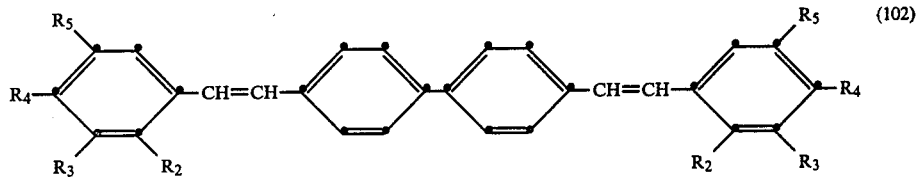

listed in Table I are obtained analogously by reacting 4,4'-bis-(dimethoxyphosphonomethyl)-biphenyl with corresponding aldehydes.

phase is dried over sodium sulfate. The solvent is evaporated off and the residue is subjected to fractional distillation under a high vacuum. After separating off the

TABLE I

| Formula | $R_2$ | $R_3$ | $R_4$ | $R_5$ | Melting point (°C.) |
|---|---|---|---|---|---|
| (103) | —O(CH$_2$)$_3$—N(CH$_3$)$_2$ | H | H | H | 131° |
| (104) | —O(CH$_2$)$_2$—N(CH$_3$)$_2$ | H | H | H | 165° |
| (105) | —O(CH$_2$)$_2$—N⟨morpholino⟩ | H | H | H | 158° |
| (106) | —O(CH$_2$)$_2$—N⟨piperidino⟩ | H | H | H | 142° |
| (107) | —O(CH$_2$)$_2$—N⟨pyrrolidino⟩ | H | H | H | 148° |
| (108) | —O(CH$_2$)$_3$—N(C$_2$H$_5$)$_2$ | H | H | H | 135° |
| (109) | —O(CH$_2$)$_3$—N(CH$_3$)$_2$ | —OCH$_3$ | H | H | 93° |
| (110) | —O(CH$_2$)$_3$—N(CH$_3$)$_2$ | H | H | Cl | 132° |
| (111) | —O(CH$_2$)$_3$—N(CH$_3$)$_2$ | H | H | CH$_3$ | 108° |
| (112) | H | —O(CH$_2$)$_2$—N(C$_2$H$_5$)$_2$ | H | H | 174° |
| (113) | H | H | —O(CH$_2$)$_2$—N(C$_2$H$_5$)$_2$ | H | 291° |
| (114) | —S(CH$_2$)$_2$—N(CH$_3$)$_2$ | H | H | H | 145° |
| (115) | —OCH$_2$—⟨pyridyl⟩ | H | H | H | 239° |
| (116) | —CH$_2$N(CH$_3$)$_2$ | H | H | H | 164° |

The aldehyde of the formula

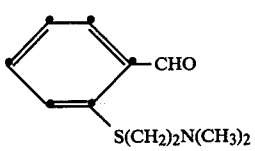

(117)

which is required for the preparation of the compound of the formula (114), can be prepared as follows: after displacing the air by nitrogen, 100 g of approximately 85% pure dimethylamino-ethanethiol hydrochloride are added, with vigorous stirring and cooling, to a mixture of 61.7 g of 88% pure potassium hydroxide in 54.3 g of water and 60 ml of dimethylsulfoxide at a rate such that the temperature does not rise above 20° C. 57.2 g of o-chlorobenzaldehyde are then allowed to run in dropwise and the temperature is kept at 60° C. for 2 hours and then at 80° C. for 2 hours. After cooling to room temperature, 300 ml of methylene chloride and 300 ml of water are added, the whole is mixed thoroughly, the two layers are allowed to separate and the organic phase is dried over sodium sulfate. The solvent is evaporated off and the residue is subjected to fractional distillation under a high vacuum. After separating off the first runnings, 18.6 g of a yellowish liquid with a boiling point of 97°–106° C./0.03 mbar and a purity of 79.3% are obtained.

EXAMPLE 2

Example 1 is repeated using a mixture (200) of the two isomeric aldehydes

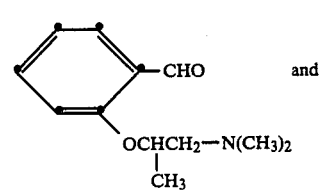

(200a) and

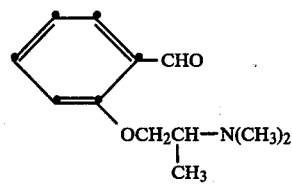
(200b)

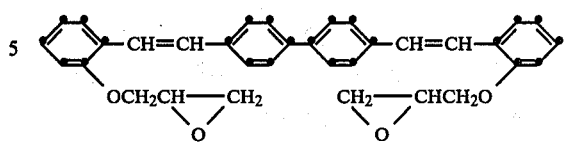
(301)

in place of an aldehyde which is a single compound. A mixture of isomers (201) is obtained which comprises the two symmetrical compounds of the formulae (201a) and (201b) and the asymmetrical compound of the formula (201c) and has a melting point of 122°–130° (after recrystallisation from nonane):

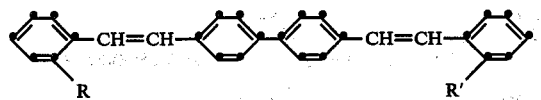

R=R' = —OCHCH₂—N(CH₃)₂  (201a)
       |
       CH₃

R=R' = —OCH₂CH—N(CH₃)₂  (201b)
          |
          CH₃

R = —OCHCH₂—N(CH₃)₂    R' = —OCH₂CH—N(CH₃)₂  (201c)
       |                        |
       CH₃                      CH₃

The mixture of the isomers of the aldehydes of the formula (200) is obtained by reacting salicylaldehyde with 2-chloro-1-dimethyl-aminopropane hydrochloride by the method of Example 1, formula (100).

EXAMPLE 3

20.6 g of 4,4'-bis-(dimethoxyphosphonomethyl)biphenyl (purity 96.9%) and 20.9 of the compound of the formula

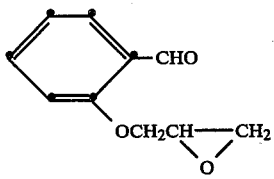
(300)

(purity 89.9%) are reacted by the method of Example 1 in 150 ml of dimethylformamide. After recrystallisation from xylene, 22.5 g of the compound of the formula are obtained in the form of pale yellow crystals with a melting point of 208°–210° C.

8.05 g of this compound are dissolved in 30 ml of dimethylformamide at 115° C., with stirring, and this solution is added dropwise to a solution of 30 ml of alcoholic 33% dimethylamine, the temperature being allowed to fall to 80° C. The reaction mixture is stirred for a further 2 hours at 80° C. and cooled and 60 ml of water are added. The product which has precipitated is filtered off with suction, washed repeatedly with water and dried in vacuo at 100° C. 9.3 g of the compound of the formula

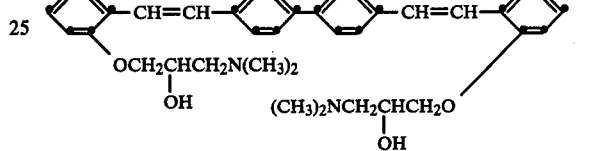
(302)

are obtained in the form of pale yellow crystals with a melting point of 140°–142° C. (after recrystallisation from nonane).

EXAMPLE 4

16.3 g of the compound of the formula

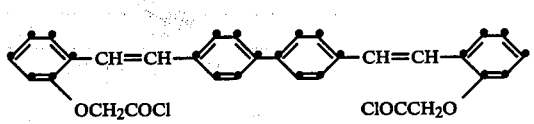
(400)

(German Offenlegungsschrift 2,209,128) and 25.5 g of 3-dimethylaminopropyl-1-amine are stirred in 250 ml of chlorobenzene under reflux. The solution is filtered hot with bleaching earth to give a clear filtrate and the latter is concentrated and allowed to cool. The product which has precipitated is filtered off with suction, washed with chlorobenzene and dried. 17.4 g of the compound of the formula

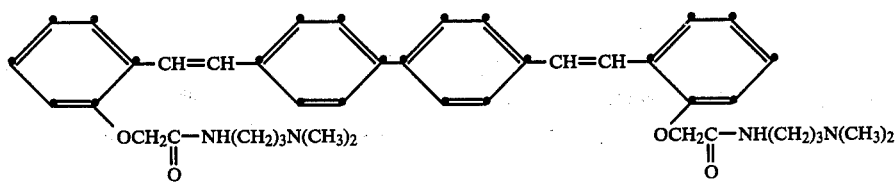
(401)

with a melting point of 226°–227° C. are obtained.

If the compound of the formtula (400) is reacted with 2-dimethylaminoethanol in accordance with Example 14, the compound of the formula

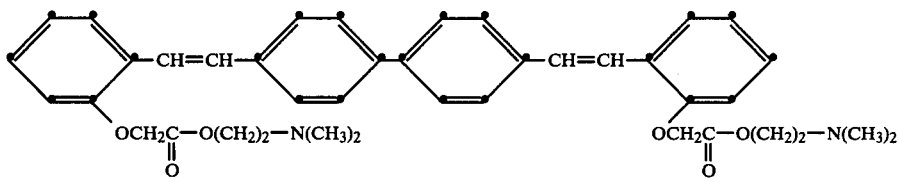
(402)

is obtained; when dissolved in dimethylformamide, this compound displays violet-blue fluorescence in daylight.

EXAMPLE 5

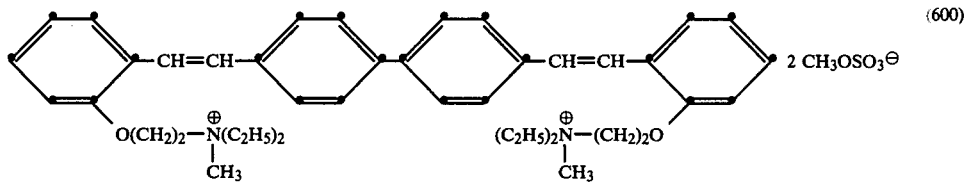
(600)

The compounds of the formula

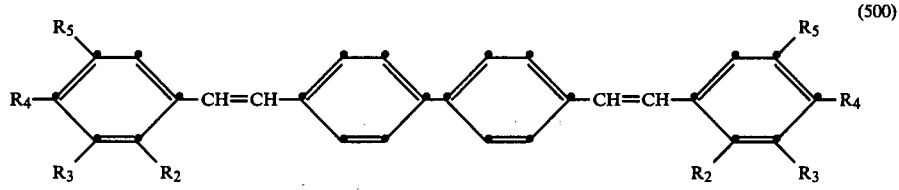
(500)

listed in Table II are obtained in a manner similar to that described in Example 1.

precipitated is filtered off with suction and washed repeatedly with methyl ethyl ketone. After drying in vacuo at 100° C., 8.2 g of the compound of the formula which still contains about ½ mol of water of crystallisation, is obtained in the form of pale yellow crystals with a melting point of 235°–238° C.

TABLE II

| Formula | $R_1$ | $R_2$ | $R_3$ | $R_4$ | $R_5$ |
|---|---|---|---|---|---|
| (501) | H | —Cl | —O(CH₂)₂—N(C₂H₅)₂ | H | H |
| (502) | H | —Cl | H | —O(CH₂)₂—N(C₂H₅)₂ | H |
| (503) | H | —O(CH₂)₂—N(C₂H₅)₂ | —Cl | H | —Cl |
| (504) | H | —O(CH₂)₂—N(C₂H₅)₂ | H | —(CH₂)₃— | |
| (505) | H | —O(CH₂)₂—N(C₂H₅)₂ | H | —(CH₂)₄— | |
| (506) | H | H | H | —O(CH₂)₃—N(CH₃)₂ | H |
| (507) | H | —O(CH₂)₂—N(C₂H₅) | —CH₂CH=CH₂ | H | H |
| (508) | H | CH₃ | H | —O(CH₂)₂—N(C₂H₅)₂ | —CH(CH₃)₂ |
| (509) | H | —O(CH₂)₂—N(C₂H₅)₂ | —CH₃ | H | —CH₃ |
| (510) | H | —O(CH₂)₂—N(C₂H₅)₂ | H | CH₃ | —Cl |

EXAMPLE 6

2.5 ml of dimethyl sulfate are added dropwise to a solution of 5.9 g of the compound of the formula (101) in 50 ml of methyl ethyl ketone, with stirring, at about 70° C. The mixture is heated under reflux for a further 1 hour and allowed to cool and the product which has It is also possible to use chlorobenzene as the solvent, in place of methyl ethyl ketone.

The compounds of the formula

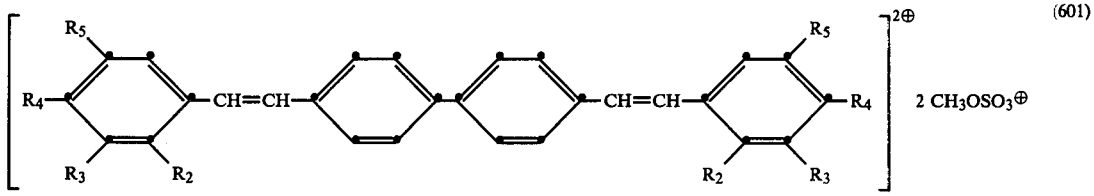
(601)

listed in Table III below are obtained in an analogous manner from the compounds described in Table I and the compounds of the formula (302) and (401).

TABLE III

| Formula | R₂ | R₃ | R₄ | R₅ | Melting point °C. |
|---|---|---|---|---|---|
| (602) | $-O(CH_2)_3-N(CH_3)_3$ | H | H | H | 263° |
| (603) | $-O(CH_2)_2-N(CH_3)_3$ | H | H | H | 285° |
| (604) | $-O(CH_2)_2-N(CH_3)(morpholino)$ | H | H | H | 227° |
| (605) | $-O(CH_2)_2-N(CH_3)(piperidino)$ | H | H | H | 197° |
| (606) | $-O(CH_2)_2-N(CH_3)(pyrrolidino)$ | H | H | H | 244° |
| (607) | $-O(CH_2)_3-N(CH_3)(C_2H_5)_2$ | H | H | H | 229° |
| (608) | $-OCH_2CH(OH)CH_2N(CH_3)_3$ | H | H | H | 234° |
| (609) | $-O(CH_2)_3-N(CH_3)_3$ | $-OCH_3$ | H | H | 264° |
| (610) | $-O(CH_2)_3-N(CH_3)_3$ | H | H | Cl | 289° |
| (611) | $-O(CH_2)_3-N(CH_3)_3$ | H | H | CH₃ | 236° |
| (612) | H | $-O(CH_2)_2-N(CH_3)(C_2H_5)_2$ | H | H | 210° |
| (613) | H | H | $-O(CH_2)_2-N(CH_3)(C_2H_5)_2$ | H | 235° |
| (614) | $-S(CH_2)_2-N(CH_3)_3$ | H | H | H | 283° |
| (615) | $-OCH_2-(4-methylphenyl)$ | H | H | H | 247° |
| (616) | $-CH_2N(CH_3)_3$ | H | H | H | 274° |
| (617) | $-OCH_2C(O)-NH(CH_2)_3-N(CH_3)_3$ | H | H | H | 228° |

For the preparation of the compounds of the formulae (613) and (617), chloroform and, respectively, dioxan are used in place of methyl ethyl ketone to dissolve the starting materials and the reaction is carried out under reflux.

EXAMPLE 7

The mixture of isomers of the formula (200) is quaternised by the method of Example 6. A mixture of the isomers of the formula (700) is obtained which comprises the two symmetrical compounds (700a) and (700b) and the asymmetrical compound of the formula (700c)

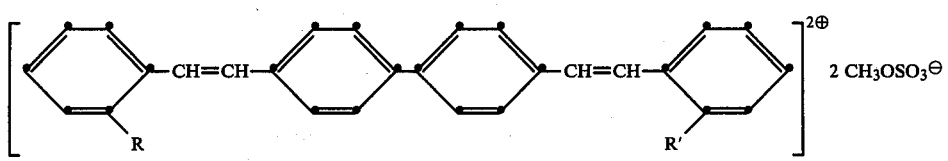

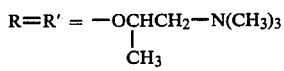 (700a)

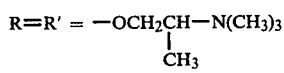 (700b)

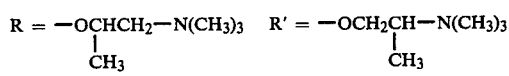 (700c)

and contains about 1 mol of water of crystallisation. Melting point 272°–285° C.

EXAMPLE 8

1.0 ml of dimethyl sulfate is added dropwise to a solution of 5.6 g of the compound of the formula (103) in 50 ml of methyl ethyl ketone, with stirring, at 70° C. The mixture is refluxed for a further 1 hour and filtered hot with suction and the material on the filter is washed three times with hot methyl ethyl ketone. A mixture of the symmetrical compound of the formula (602) and of the asymmetrical compound of the formula

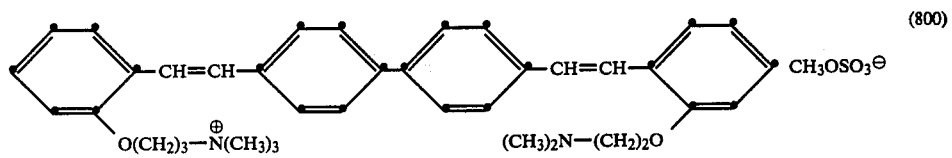

is obtained. Melting point 233°–240° C.

The compounds of the formulae (614) and

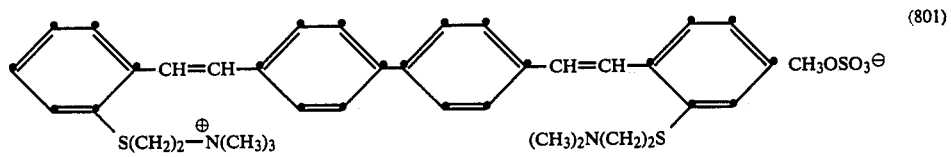

are obtained in a similar manner from (114). Melting point 249°–252° C.

EXAMPLE 9

11.2 g of the compound of the formula (103) in 25 g of dimethyl methanephosphonate are stirred for 2 hours at 120° C., during which time the end product crystallises out. The reaction mixture is diluted with 25 ml of methyl ethyl ketone, allowed to cool and filtered with suction and the residue is washed repeatedly with methyl ethyl ketone. After drying in vacuo at 100° C., this yields 13.1 g of the compound of the formula

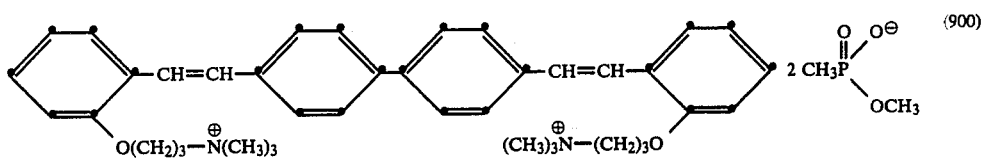

which contains ½ mol of water of crystallisation and has a melting point of 243° C. (with decomposition).

The compound of the formula

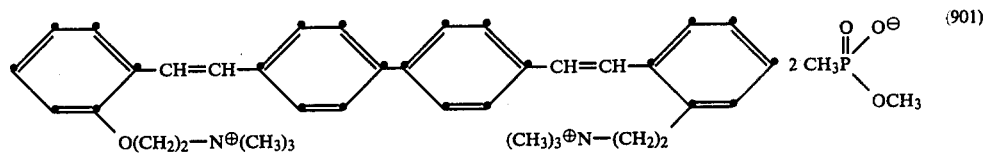

which crystallises with about 2 mols of water of crystallisation and has a melting point of 222°–235° C., and the compound of the formula

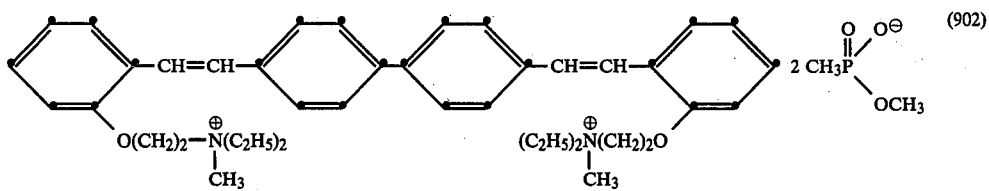

which crystallises with about 1½ mols of water of crystallisation and has a melting point of 165°-178° C., are obtained in a similar manner from (104) and (101) respectively.

EXAMPLE 10

Trimethylamine is passed into a solution of 5.4 g of the compound of the formula

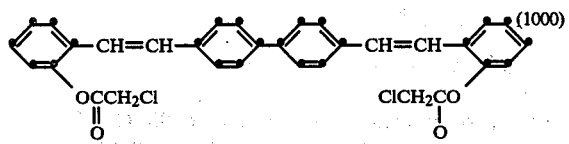

in 100 ml of chlorobenzene, at 120° C., until the solution is saturated (this takes about 10 minutes). The solution is allowed to cool to room temperature and the product which has precipitated is filtered off with suction, washed repeatedly with chlorobenzene and methyl ethyl ketone and dried in vacuo at 100° C. 6.5 g of the compound of the formula

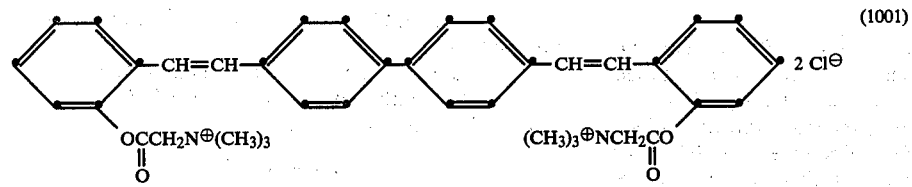

with a melting point of 175° C. (with decomposition) are obtained.

The starting material of the formula (1000) is obtained as follows:

After displacing the air by nitrogen, 159.3 g of a methanolic 30.5% solution of sodium methylate are added dropwise, with stirring, to a solution of 42.0 g of biphenyl-4,4'-dialdehyde and 197.7 g of the compound of the formula

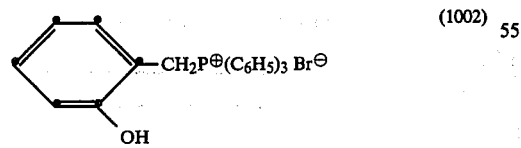

in 600 ml of dimethylformamide at a rate such that the temperature does not rise above 40° C. The temperature is kept at 40°-45° C. for 2 hours and the reaction mixture is allowed to cool and is poured into 3,000 ml of water, with stirring. The resulting mixture is neutralised to pH 8, by passing in carbon dioxide until the mixture is saturated or by adding solid carbon dioxide, and the reaction product precipitates as a resin. The aqueous phase is decanted off and the reaction product is stirred with 3,000 ml of water, filtered off with suction and washed repeatedly with water. The moist residue is taken up in 1,000 ml of boiling methyl ethyl ketone, the solution is filtered hot with 0.4 g of bleaching earth to give a clear filtrate and the latter is evaporated to half its volume. The residual solution is cooled to 0° C. and the product which has crystallised out is filtered off with suction, washed with twice 50 ml of cooled methyl ethyl ketone and dried in vacuo at 100° C. 34.7 g of the compound of the formula

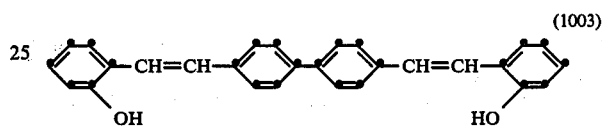

are obtained. Melting point 280°-287° C. (after recrystallisation from methyl ethyl ketone).

15.6 g of the compound of the formula (1003) in 40 ml of chloroacetyl chloride are stirred overnight under reflux and at the end of this time everything has dissolved. 40 ml of cyclohexane are added, the mixture is allowed to cool and the product which has precipitated is filtered off with suction, washed repeatedly with cyclohexane and dried in vacuo at 100° C. After recrystallisation from perchloroethylene, 13.4 g of the compound of the formula (1000) are obtained in the form of pale yellow crystals. Melting point 182°-185° C. (after recrystallisation from xylene).

EXAMPLE 11

Example 10 is repeated using the isomer of the formula

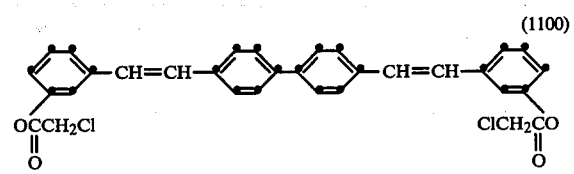

Melting point 240°-241° (from chlorobenzene)
in place of the compound of the formula (1000). The compound of the formula

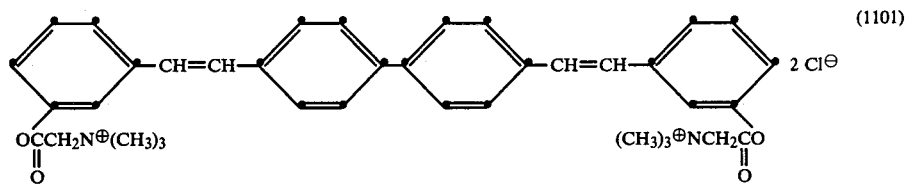

Melting point 259°–275° C. is obtained.

When this example is repeated using pyridine (3.2 ml) in place of trimethylamine, 4.5 g of the compound of the formula

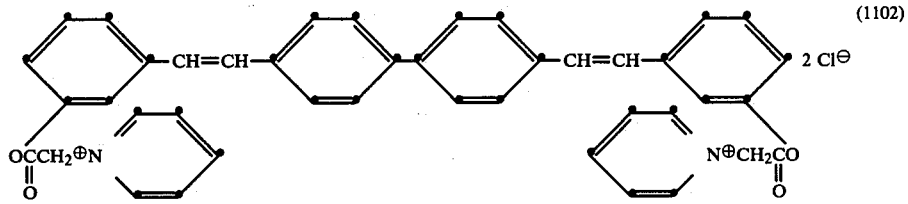

Melting point 260°–288° C. are obtained after a reaction time of 2½ hours.

The starting material of the formula (1100) is obtained as follows:

After displacing the air by nitrogen, 797 g of a methanolic 30.5% solution of sodium methylate are added dropwise, with stirring, to a solution of 418 g of 4,4'-bis-(dimethoxyphosphonomethyl)-biphenyl (purity 96.9%) and 256.2 g of 3-hydroxybenzaldehyde in 1,000 ml of dimethylformamide at a rate such that the temperature does not rise above 40° C. The temperature is kept at 40°–45° C. for 4 hours, the mixture is cooled and 2000 ml of water are added. The resulting mixture is neutralised to a pH of about 8, by passing in carbon dioxide until the mixture is saturated or by adding solid carbon dioxide, and the product which has precipitated is filtered off with suction, washed repeatedly with water and isopropanol and dried in vacuo at 100° C. (317.9 g). After recrystallisation from dioxan the compound of the formula

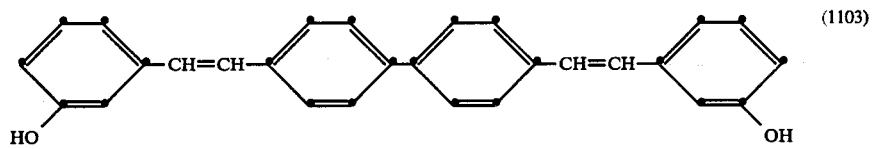

Melting point 315°–325° C. is obtained in the form of pale yellow crystals.

This is converted to the compound of the formula (1100) by the method given in Example 10 for the compound of the formula (1000).

EXAMPLE 12

The compounds of the formula

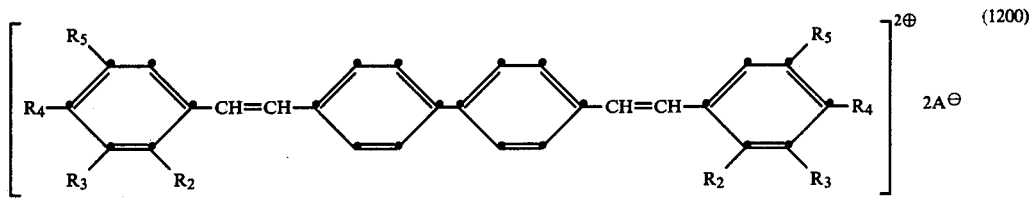

listed in Table IV are obtained by a method similar to that described in Examples 6, 9 or 10.

TABLE IV

| Formula | $R_2$ | $R_3$ | $R_4$ | $R_5$ | A |
|---|---|---|---|---|---|
| (1201) | Cl | —O(CH$_2$)$_2$—N(C$_2$H$_5$)$_2$<br>\|<br>CH$_3$ | H | H | CH$_3$OSO$_3$ |
| (1202) | Cl | H | —O(CH$_2$)$_2$—N(C$_2$H$_5$)$_2$<br>\|<br>CH$_3$ | H | " |
| (1203) | CH$_3$<br>\|<br>—O(CH$_2$)$_2$—N(C$_2$H$_5$)$_2$ | —Cl | H | —Cl | " |

TABLE IV-continued

| Formula | R₂ | R₃ | R₄ | R₅ | A |
|---|---|---|---|---|---|
| (1204) | $-O(CH_2)_2-N(C_2H_5)_2$ with $CH_3$ | H | | $-(CH_2)_3$ | " |
| (1205) | $-O(CH_2)_2-N(C_2H_5)_2$ with $CH_3$ | H | | $-(CH_2)_4$ | " |
| (1206) | H | H | $-O(CH_2)_3-N(CH_3)_3$ | H | " |
| (1207) | $-O(CH_2)_2-N(C_2H_5)_2$ with $CH_3$ | $-CH_2CH=CH_2$ | H | H | " |
| (1208) | $-CH_3$ | H | $-O(CH_2)_2-N(C_2H_5)_2$ with $CH_3$ | $-CH(CH_3)_2$ | " |
| (1209) | $-O(CH)_2-N(C_2H_5)_2$ with $CH_3$ | $-CH_3$ | H | $-CH_3$ | " |
| (1210) | $-O(CH_2)_2-N(C_2H_5)_2$ with $CH_3$ | H | $-CH_3$ | $-Cl$ | " |
| (1211) | $-OCH_2CO(CH_2)_2-N(CH_3)_3$ | H | H | H | " |
| (1212) | $-O(CH_2)_2-N(C_2H_5)_3$ | H | H | H | Br |
| (1213) | $-O(CH_2)_2-N(C_2H_5)_2$ with $CH_2C_6H_5$ | H | H | H | Cl |
| (1214) | $-O(CH_2)_2-N(C_2H_5)_2$ with $CH_2COOCH_3$ | H | H | H | Cl |
| (1215) | $-O(CH_2)_2-N(C_2H_5)_2$ with $CH_3$ | H | H | H | $CH_3-C_6H_4-SO_3$ |
| (1216) | $-O(CH_2)_2-N(C_2H_5)_2$ with $CH_2CN$ | H | H | H | Cl |
| (1217) | $-O(CH_2)_3-N(CH_3)_2$ with $C_2H_5$ | H | H | H | $C_2H_5OSO_3$ |
| (1218) | H | H | $-CH_2N(CH_3)_3$ | H | Cl |
| (1219) | $-O(CH_2)_3-N(CH_3)_2$ with $CH_2CH=CH_2$ | H | H | H | Cl |
| (1220) | $-O(CH_2)_3-N(CH_3)_2$ with $CH_2CH_2OH$ | H | H | H | $CH_3COO$ |
| (1221) | $-O(CH_2)_3N(CH_3)_2$ with $CH_2CH(OH)-CH_3$ | H | H | H | HCOO |

EXAMPLE 13

6.1 g of the compound of the formula

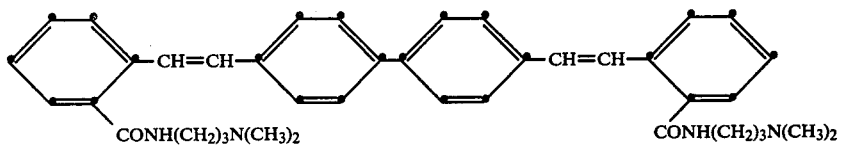

(1300)

are suspended in 250 ml of methyl ethyl ketone at 45° C., with stirring. After adding 2.5 ml of dimethyl sulfate, the reaction mixture is heated to the boil and refluxed for 1½ hours. After cooling to room temperature the product which has crystallised out is filtered off with suction, washed with methyl ethyl ketone and dried in vacuo at 60°–70° C. This yields 8.1 g of the compound of the formula

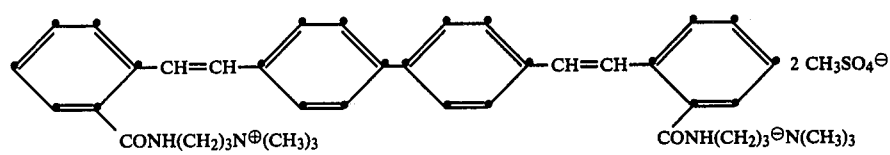

(1301)

with a melting point of 196°–216° C.

EXAMPLE 14

102 g of the compound of the formula (1400)

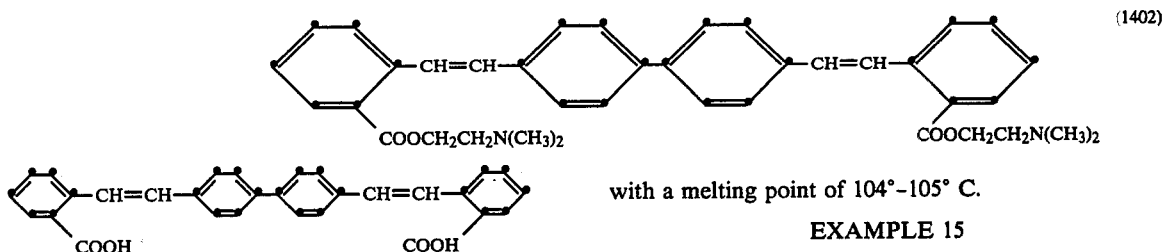

are suspended at room temperature in 1,000 ml of chlorobenzene and 2 ml of dimethylformamide, with stirring. 125 ml of thionyl chloride are added dropwise in the course of 10 minutes and the reaction mixture is heated to 80° C. and stirred at 80°–85° C. for 3 hours. After cooling to room temperature, the product which has crystallised out is filtered off with suction, washed with hexane and dried in vacuo at 80°–85° C. This yields 105.7 g of the compound of the formula (1401)

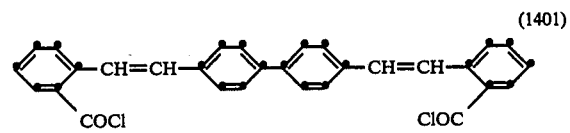

with a melting point of 212° C. (with decomposition).

24.2 g of the compound of the formula (1401) are suspended at 2° C. in 250 ml of 1,2-dimethoxyethane, with stirring. 35.7 g of 2-dimethylamino-ethanol are then added dropwise in the course of 15 minutes and the reaction mixture is stirred for 23 hours at 2°–5° C. The temperature of the suspension i then allowed to rise to 20° C. in the course of 45 minutes and the suspension is stirred for a further 4 hours at 20°–25° C. The reaction mixture is poured into 2,500 ml of water and the product is filtered off with suction and dried in vacuo at 50°–60° C.

The crude product thus obtained is twice recrystallised from a mixture of 175 ml of ethanol and 75 ml of water with the aid of active charcoal. This yields 19.1 g of the compound of the formula (1402)

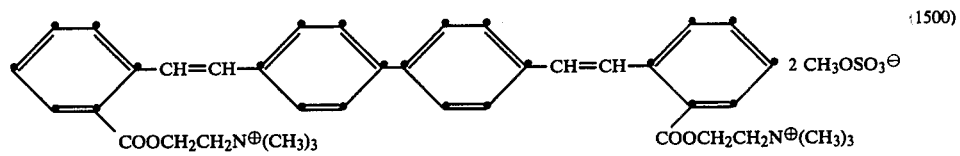

with a melting point of 104°–105° C.

EXAMPLE 15

5.9 g of the compound of the formula (1402) are dissolved in 250 ml of methyl ethyl ketone at 45° C., with stirring. After adding 2.5 ml of dimethyl sulfate, the mixture is heated to the boil and refluxed for 3½ hours. After cooling to room temperature, the product is filtered off with suction, washed with methyl ethyl ketone and dried in vacuo at 60°–70° C. This yields 7.6 g of the compound of the formula (1500)

with a melting point of 280°–285° C.

EXAMPLE 16

Using a liquor ratio of 1:20, a bleached cotton fabric is treated on a dyeing apparatus with an aqueous liquor which contains 0.1% of the fluorescent brightener of the formula (600), (602) to (606), (608), (617), (700 a-c), (800), (900) or (901), based on the weight of the cotton, and 5 g/l of sodium sulfate.

The application is carried out in accordance with the following temperature programme: 15 minutes at 20°–50° C. and 15 minutes at 50° C.

The cotton fabric is then rinsed for 20 seconds in running softened water and dried at 70° C. in a drying cabinet. The cotton fabric treated in this way has a good white effect.

EXAMPLE 17

A bleached cotton fabric is padded at room temperature with an aqueous liquor which contains 1 g/l of the fluorescent brightener of the formula (600), (602) to (606), (608), (617), (700 a-c), (800), (900) or (901). The liquor pick-up is 75%.

The fabric is then dried for 30 seconds at 70° C. on a thermofixing apparatus.

The cotton fabric treated in this way has a good white effect.

EXAMPLE 18

Using a liquor ratio of 1:20, a polyacrylonitrile fabric (Orlon 75) is treated on a dyeing apparatus with an aqueous liquor which contains 0.1% of the fluorescent brightener of the formula (101), (103)–(107), (600), (602)–(606), (610), (700 a-c), (800) or (901), based on the weight of goods, 1 g/l of an adduct of 35 mols of ethylene oxide with 1 mol of stearyl alcohol and 1.5 ml/l of 85% formic acid.

The application is carried out in accordance with the following temperature programme: 30 minutes at 40°–97° C., 30 minutes at 97° C. and 15 minutes at 97°–40° C.

The polyacrylonitrile fabric is then rinsed for 20 seconds in running softened water and dried at 70° C. in a drying cabinet. The fabric treated in this way has a good white effect.

EXAMPLE 19

Using a liquor ratio of 1:20, a bleached cotton fabric is treated for 15 minutes in a warm, aqueous soft-rinse liquor which is at 30° C. and contains, per liter, 0.2 g of quaternary dimethyldistearyl-ammonium chloride and 0.01 g of the fluorescent brightener of the formula (600), (602)–(608), (700 a-c), (900) or (901).

The cotton fabric is then rinsed for 5 seconds in running drinking water and dried at 70° C. in a drying cabinet. The cotton fabric treated in this way has a good white effect.

EXAMPLE 20

Using a liquor ratio of 1:20, a bleached cotton fabric is washed for 15 minutes in a warm aqueous liquor which is at 40° C. and contains, per liter, 0.5 g of an adduct of 10 mols of ethylene oxide with 1 mol of stearyl alcohol and 0.01 g of the fluorescent brightener of the formula (600), (602)–(609), (617), (700 a-c), (800), (900) or (901).

The cotton fabric is then rinsed for 20 seconds in running drinking water and dried at 70° C. in a drying cabinet. The cotton fabric treated in this way has a good white effect.

EXAMPLE 21

Using a liquor ratio of 1:20, a modified polyacrylonitrile fabric (Courtelle ®) is treated on a dyeing apparatus with an aqueous liquor which contains 0.1% of the fluorescent brightener of the formula (101), (103)–(107), (600), (602)–(606), (610), (700 a-c), (800) or (901), based on the weight of goods, 1 g/l of oxalic acid, 0.25 g/l of a polyphosphate as a complexing agent and 0.125 g/l of sodium metabisulfite. The application is carried out in accordance with the following temperature programme: 30 minutes at 40°–97° C., 30 minutes at 97° C. and 15 minutes at 97°–40° C.

The polyacrylonitrile fabric is then rinsed for 30 seconds in running softened water and dried at 70° C. in a drying cabinet. The fabric treated in this way has a good white effect.

EXAMPLE 22

Using a liquor ratio of 1:20, a polyamide-6 fabric is treated on a dyeing apparatus with an aqueous liquor which contains 0.3%, based on the weight of fabric, of a compound of the formula (101), (103)–(107), (109), (200) or (302), 1 g/l of an adduct of 1 mol of stearyl alcohol with 35 mols of ethylene oxide, 1 g/l of an adduct of 1 mol of p-tert.-octylphenol with 8 mols of ethylene oxide and 0.5 g/l of sodium phosphate buffer. The application is carried out in accordance with the following temperature programme: 50°–100° C. in the course of 10 minutes, 100° C. for 20 minutes and 100°–50° C. in the course of 5 minutes.

The fabric is then rinsed in softened cold water and dried at 60° C. The fabric treated in this way has a good white effect.

EXAMPLE 23

Using a liquor ratio of 1:20, a polyamide-6 fabric is treated on a dyeing apparatus with an aqueous liquor which contains 0.3%, based on the weight of fabric, of a compound of the formula (600), (602)–(607), (700 a-c), (800), (900) or (901), 1 g/l of an adduct of 1 mol of stearyl alcohol with 35 mols of ethylene oxide, 1 g/l of an adduct of 1 mol of p-tert.-octylphenol with 8 mols of ethylene oxide and 0.5 g/l of sodium phosphate buffer. The application is carried out in accordance with the following temperature programme: 30°–60° C. in the course of 10 minutes and 60° C. for 20 minutes. The fabric is then rinsed in softened cold water and dried at 60° C. The fabric treated in this way has a good white effect.

EXAMPLE 24

5 g of fibrous material (consisting of bleached sulfite cellulose and bleached beech cellulose, 1:1) in 50 ml of water are mixed for 15 minutes in a mixer with 150 ml of fluorescent brightener solution containing 2.5 mg, corresponding to a concentration of 0.05%, of the fluorescent brightener of the formula (600), (602)–(606), (900) or (901). 1.5% by weight of size, for example Bewoidleim ®, and 2.5% by weight of aluminium sulfate (based on the weight of dried fibre) are then added and the mixture is diluted to 1,000 ml with water of about 10° German hardness. This fibre suspension is used to form a sheet of paper and this has a good white effect.

EXAMPLE 25

5 g of fibrous material (consisting of bleached sulfite cellulose and bleached beech cellulose, 1:1) in 150 ml of water containing 5 mg of a cationic polyetheramine are mixed for 15 minutes in a mixer with 50 ml of fluorescent brightener solution containing 2.5 mg, corresponding to a concentration of 0.05%, of the fluorescent brightener of the formula (600), (602)–(606), (900) or (901). 1.5% by weight of size, for example Bewoidleim®, 2.5% by weight of aluminium sulfate and 0.1% of a cationic polyether-amine (based on the weight of dry fibre) are then added and the mixture is diluted at 1,000 ml with water of about 10° German hardness. This fibre suspension is used to form a sheet of paper and this has a good white effect.

EXAMPLE 26

5 g of fibrous material (consisting of bleached sulfite cellulose and bleached beech cellulose, 1:1) in 150 ml of water containing 5 mg of polyethyleneimine are mixed for 15 minutes in a mixer with 50 ml of fluorescent brightener solution containing 2.5 mg, corresponding to a concentration of 0.05%, of the fluorescent brightener of the formula (600), (602)-(606), (900) or (901). 1.5% by weight of size, for example Bewoidleim®, 2.5% by weight of aluminium sulfate and 0.1% of a polyethyleneimine (based on the weight of dry fibre) are then added and the mixture is diluted to 1,000 ml with water of about 10° German hardness. This fibre suspension is used to form a sheet of paper and this has a good white effect.

EXAMPLE 27

An intimate mixture of 100 parts of polyvinyl chloride, 3 parts of stabiliser (Advastat BD 100®; Ba/Cd complex), 2 parts of titanium dioxide, 59 parts of dioctyl phthalate and 0.01 to 0.2 part of a compound of the formula (101), (103)-(107) or (201) is rolled out on a calander at 150° to 155° C. to give a film. The opaque polyvinyl chloride film thus obtained has a substantially higher whiteness than a film which does not contain the fluorescent brightening agent.

EXAMPLE 28

A concentrated liquid detergent is prepared by mixing the following components:

| | % by weight |
|---|---|
| ethoxylated alcohols ($C_{12}$–$C_{13}$ alcohol with 6.5 mols of ethylene oxide) | 60.0 |
| 1-methyl-1-oleylamidomethyl-2-oleyl-imidazolinium methosulfate | 26.7 |
| the compound of the formula (600) (602)-(609), (700), (800), (900) or (901) | 0.3 |
| water | 12.0 |
| conventional additives | 1.0 |

2 kg of bleached cotton fabric are washed for 10 minutes at 60° C. in 60 liters of water of 100 ppm hardness, which contains 50 to 60 g of the above detergent. After rinsing and drying, the fabric has a powderful white effect and a soft handle. If 0.2 g/l of active chlorine in the form of sodium hypochlorite is also added to the wash liquor described above and the procedure described is repeated, good effects are again obtained.

Similar results are obtained using, in place of the above detergent, a liquid detergent of the following composition:

| | % by weight |
|---|---|
| ethoxylated alcohols ($C_{12}$–$C_{13}$ alcohol with 6.5 mols of ethylene oxide) | 55.0 |
| 1-methyl-1-tallow-amidoethyl-2-tallow-imidazolinium methosulfate | 26.0 |

-continued

| | % by weight |
|---|---|
| the compound of the formula (600), (602)-(609), (700), (800), (900) or (901) | 0.3 |
| water | 13.0 |
| isopropanol | 5.0 |
| conventional additives | 0.7 | or another liquid detergent containing nonionic surfactants and cationic substances, for example "Perwoll® liquid" or Samtess®, which are available commercially, and to which the fluorescent brighteners according to the invention have been admixed.

EXAMPLE 29

A liquid detergent is prepared by mixing the following components:

| | % by weight |
|---|---|
| ethoxylated alcohols ($C_{14}$-$C_{15}$ alcohol with 7 mols of ethylene oxide) | 12.0 |
| ethoxylated alcohols ($C_{12}$-$C_{13}$ alcohol with 6.5 mols of ethylene oxide) | 12.0 |
| non-cured di-tallow-dimethyl-ammonium chloride | 6.4 |
| ethanol | 15.0 |
| sodium bicarbonate | 0.25 |
| the compound of the formula (600), (602)-(609), (700), (800), (900) or (901) | 0.41 |
| conventional addditives | 0.41 |
| water | 53.53 |

A cotton fabric treated as described in Example 28 has a powerful white effect and a soft handle.

What is claimed is:

1. A distyrylbiphenyl of the formula

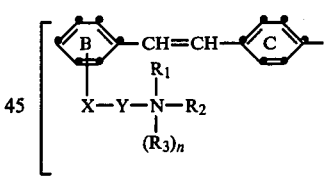

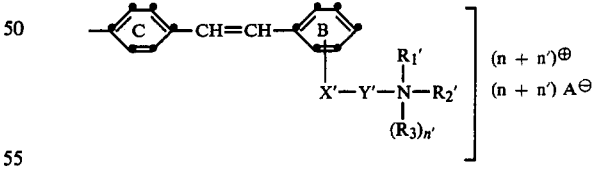

in which X and X' independently of one another are sulfur, —O—$C_{1\text{-}3}$-alkylene—COO— or —OCO—, Y and Y' independently of one another are $C_{1\text{-}20}$-alkylene or $C_1$–$C_{20}$-hydroxyalkylene, $R_1$, $R_1'$, $R_2$ and $R_2'$ independently of one another are $C_{1\text{-}8}$-alkyl or $C_{3\text{-}4}$-alkenyl, $R_3$ is hydrogen, $C_{1\text{-}4}$-alkyl or $C_{3\text{-}4}$-alkenyl, or $R_1$ and $R_2$ or $R_1'$ and $R_2'$ together with the N atom to which they are attached, is pyrrolidine, piperidine, hexamethyleneimine or morpholine, or $R_1$ and $R_2$, or $R_1'$ and $R_2'$, together with $R_3$ and the N atom to which they are attached, are pyridine or picoline, $A^\ominus$ is a colorless anion and n and n' independently of one another are 0 or 1, the benzene rings B and C can also be substituted by halogen, $C_{1-4}$-alkyl, $C_{3-4}$-alkenyl or $C_{1-3}$-alkoxy, and the benzene rings B can also be substituted by a trimethylene or tetramethylene group.

2. A distyrylbiphenyl of claim 1 of the formula

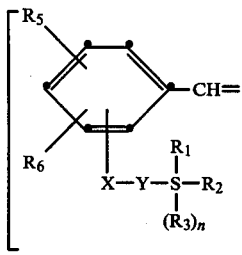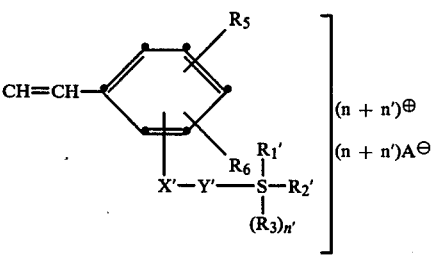

wherein X and X' are identical, Y and Y' are independently $C_{1-4}$-alkylene or hydroxypropylene, $R_1$ and $R_1'$ are identical, $R_2$ and $R_2'$ are identical, $R_1$ and $R_2$ are independently $C_{1-4}$-alkyl, $R_3$ is hydrogen, $C_{1-4}$-alkyl or $C_{3-4}$-alkenyl, or $R_1$ and $R_2$ or $R_1'$ and $R_2'$ together with the N atom to which they are attached, is pyrrolidine, piperidine, hexamethyleneimine or morpholine, or $R_1$ and $R_2$, or $R_1'$ and $R_2'$, together with $R_3$ and the N atom to which they are attached, are pyridine or picoline, $R_5$ and $R_6$ are independently hydrogen, chlorine, $C_{1-4}$-alkyl, $C_{3-4}$-alkenyl or $C_{1-3}$-alkoxy provided that only one of $R_5$ and $R_6$ is $C_{3-4}$-alkenyl, and $R_5$ and $R_6$ together can be a trimethylene or tetramethylene group.

3. A distyrylbiphenyl of claim 1, wherein X and X', Y and Y', $R_1$ and $R_1'$, $R_2$ and $R_2'$ and n and n' are identical.

4. A distyrylbiphenyl of claim 2, wherein $Y_1$ and $Y_1'$ and n and n' are identical.

5. A distyrylbiphenyl of claim 4, wherein $R_1$ and $R_2$ are independently $C_{1-4}$-alkyl, $R_3$ is hydrogen, $C_{1-4}$-alkyl or $C_{3-4}$-alkenyl, or $R_1$ and $R_2$ together with the N atom to which they are attached, are pyrrolidine, piperidine or morpholine, or $R_1$ and $R_2$ together with $R_3$ and the N atom to which they are attached are pyridine, $R_5$ is hydrogen, chlorine, $C_{1-4}$-alkyl or $C_{1-3}$-alkoxy, and $R_6$ is hydrogen.

6. A distyrylbiphenyl of claim 1, wherein X and X' are both sulfur, Y and Y' are identical and are $C_{2-20}$-alkylene, $R_1$ and $R_1'$, $R_2$ and $R_2'$ and n and n' are identical, and $R_1$, $R_2$ and $R_3$ may not be taken together with the N atom to which they are attached to be pyridine or picoline.

7. A distyrylbiphenyl of claim 6, wherein the rings B are unsubstituted para to the vinyl substituent and the C rings are unsubstituted meta to the vinyl substituent.

* * * * *